United States Patent [19]

Malis et al.

[11] Patent Number: 4,590,934
[45] Date of Patent: May 27, 1986

[54] BIPOLAR CUTTER/COAGULATOR

[75] Inventors: Jerry L. Malis, 1030 Union Meeting Rd., Blue Bell, Pa. 19422; Leonard I. Malis, 219-44 Peck Ave., Queens, N.Y. 11427; Robert R. Acorcey, Blackwood, N.J.; David Solt, Willow Grove, Pa.

[73] Assignees: Jerry L. Malis, Blue Bell, Pa.; Leonard I. Malis, Queens, N.Y.

[21] Appl. No.: 495,906

[22] Filed: May 18, 1983

[51] Int. Cl.$^4$ ............................................. A61B 17/36
[52] U.S. Cl. ........................... 128/303.14; 128/303.17
[58] Field of Search ...................... 128/303.14, 303.17, 128/904; 340/692; 328/109

[56] References Cited

U.S. PATENT DOCUMENTS

| | | | |
|---|---|---|---|
| 2,993,178 | 7/1961 | Burger | 128/303.14 |
| 3,058,470 | 10/1962 | Seeliger et al. | 128/303.17 |
| 3,658,067 | 4/1972 | Bross | 128/303.14 |
| 3,699,967 | 10/1972 | Anderson | 128/303.14 |
| 3,885,552 | 5/1975 | Kennedy | 128/904 |
| 3,898,991 | 8/1975 | Ikuno et al. | 128/303.14 |
| 3,913,583 | 10/1975 | Bross | 128/303.14 |
| 3,929,137 | 12/1975 | Gonser | 128/303.14 |
| 3,963,030 | 6/1976 | Newton | 128/303.17 |
| 3,964,487 | 6/1976 | Judson | 128/303.14 |
| 4,038,984 | 8/1977 | Sittner | 128/303.14 |
| 4,231,372 | 11/1980 | Newton | 128/303.17 |
| 4,244,371 | 1/1981 | Farin | 128/303.17 |
| 4,245,192 | 1/1981 | Whiffen | 328/109 |
| 4,301,801 | 11/1981 | Schneiderman | 128/303.17 |
| 4,318,409 | 3/1982 | Oosten | 128/303.17 |
| 4,359,713 | 11/1982 | Tsunoda | 340/692 |
| 4,398,534 | 8/1983 | Hagiwara | 128/303.14 |
| 4,429,694 | 2/1984 | McGreevy | 128/303.17 |
| 4,438,766 | 3/1984 | Bowers | 128/303.17 |

FOREIGN PATENT DOCUMENTS 2026869 2/1980 United Kingdom ........... 128/303.14

Primary Examiner—Kyle L. Howell
Assistant Examiner—Ruth S. Smith
Attorney, Agent, or Firm—Seidel, Gonda, Goldhammer & Abbott

[57] ABSTRACT

A bipolar cutter/coagulator produces a coagulating waveform comprising an aperiodic sequence of damped RF bursts. The inter-burst spacing is pseudo-random, and the intra-burst RF frequency is swept between preset limits. The burst envelopes are uniform, always starting at the same preselected amplitude.

92 Claims, 22 Drawing Figures

BIPOLAR CUTTER/COAGULATOR

BACKGROUND OF THE INVENTION

The present invention is directed to a bipolar cutter/coagulator for use in surgery. The cutter/coagulator may be employed to cut and repair tissues and is particularly required for use in microsurgery.

Prior art monopolar and bipolar coagulators used spark-gap generators to produce an aperiodic sequence of radio frequency (RF) bursts having random spike components. Such waveforms produce the best coagulation. However, the initial spike of each damped burst is much higher in voltage than the rest of the burst, as a requirement for striking the arc in the spark-gap. This high initial voltage spike is responsible for undesirable sparking at the forceps tips and produces television and monitoring equipment interference.

Electronic tube or solid state coagulators generally provide regularly occurring bursts of damped sine waves, square waves, or undamped pulses as the coagulating waveform. The regular occurrence of these waveforms increases undesirable cutting or perforation of vessels during coagulation, as a result of induced molecular resonance.

The present invention simulates the aperiodic RF bursts of the spark gap systems, but the leading voltage spike in each burst is controlled, the burst envelopes are uniform from burst to burst, and the intra-burst RF frequency is randomized. The new waveform results in the elimination of molecular resonance, hence undesirable cutting or perforation during coagulation. Control of the first spike of each burst also results in marked reduction of sparking of the forceps as well as reduction of interference with other equipment in the operating room. The waveform parameters namely, inter-burst spacing, intraburst RF frequency, and the spacing between consecutive sequence of bursts, produce the smoothest coagulation, least neuromuscular stimulation, the least pitting of the forceps as well as the least charring and sticking at the forceps, and the least vascular perforation.

Monopolar coagulators have long been used in surgery. Monopolar coagulators provide a current path from a single active electrode through the patient to a return or ground plate. The highest power per tissue volume is produced at the active electrode. The most conductive path to ground receives the highest current density, so that appreciable current can be distributed in adjacent tissues. The most conductive path can be through the blood. In a small vessel being coagulated, current can flow through the blood and coagulate the parent vessel inadvertently. Moreover, use of the monopolar coagulator under saline irrigation is not feasible, since the saline rather than the desired tissue can furnish the most conductive path to ground.

Bipolar coagulator, as compared with monopolar, utilize a pair of forcep electrodes coupled by cable to isolated power outputs. The forcep blades are insulated from each other. The power output of the bipolar coagulator is isolated from ground, so that current flow is restricted to a zone between the forcep tips. Current does not flow from either forcep tip to ground. The current path geometry depends primarily on the tip size, the angle at which the tips meet, and the conductivity of the medium in which the tips are immersed. If the forceps blades are virtually parallel and are deeply immersed in saline, there can be major shunting of current through the saline despite isolation of the power output. But if the forceps blades are bowed or angled so that the tips almost meet while the parallel portion of the blades remain well-separated, current flow is restricted to the zone between the tips with little shunting through the saline.

The power output section of a bipolar cutter/coagulator should have a low output impedance to maintain uniform power at the forcep tips over a wide range of load conditions, from dry tissue to heavily irrigated tissue. The present invention provides a stiffly regulated, isolated power output with an output impedance of approximately 5-10 ohms. By contrast, the output impedances of previously available solid state systems are approximately 50-500 ohms, and even the best spark gap coagulator has an output impedance of 40-50 ohms. The lower output impedance of the present invention facilitates its use under the constant irrigation desirable for cooling and protecting adjacent delicate vessel, tissue and nerve structures.

BRIEF SUMMARY OF THE INVENTION

A bipolar cutter/coagulator comprises a waveform generator section which generates a power output waveform comprising groups of aperiodic sequences of damped bursts of high frequency (RF) signals. Each burst decays gradually from a controlled, initial amplitude. The burst decay envelopes are uniform, that is substantially identical, from burst to burst. The inter-burst spacings are pseudo-random. The frequency of the RF signal within a burst is randomized by sweeping the frequency between preset limits.

The power output terminals of the cutter/coagulator, to which the forceps are coupled, are isolated from ground and are coupled to the secondary of a step-down transformer so as to better match the output impedance to the load impedance. An AGC loop is interposed between the power output section and the waveform generator section. The power output section and the AGC loop produce substantially uniform power output over the entire range of impedances typically encountered at the forceps during surgery.

Each damped RF burst produced by the power output section is generated based on a burst of ramped analog pulses produced by the waveform generator section. The bursts of ramped analog pulses are generated in an aperiodic sequence, the spacing between bursts being pseudo-random. The frequency of the pulses within a burst is swept about a center RF frequency between preset limits. The pulses are swept in frequency in phase coherence with the rate at which the pulse amplitudes change within a burst.

The power output level is operator selectable and may be slewed up (increased power output) or down (decreased power output) under control of a programmed microprocessor and the AGC loop. Each power setting in a slewed sequence of power settings is indicated visually on an LED display and is announced by a voice synthesizer.

Operation in the Cut or Coagulation mode is operator selectable by manipulating a foot pedal switch. Operation in either mode is announced by a unique mixture of tones. Disconnection of the foot pedal switch is automatically detected and an error message is automatically displayed on the LED display to indicate the condition. The condition is also announced by the voice synthesizer.

Loss of aperiodicity of the damped RF bursts is detected internally and the condition is displayed on the LED display while being announced by the voice synthesizer.

Other malfunctions are detected internally and are also visually displayed and announced.

An object of the invention is to produce a new power output waveform for application to forceps used in electrosurgery such that the waveform power is sufficient to produce controlled coagulation without causing inadvertent cutting, perforation or other damage to tissue.

An object of the invention is to produce a new power output waveform for application to the forceps which substantially eliminates charring and sticking at the forceps.

An object of the invention is to generate a power output waveform having the aperiodicity of a spark gap waveform without using the spark gap.

An object of the invention is to simulate the aperiodicity of the spark gap waveform while eliminating the uncontrolled initial spike which characterizes each RF burst of the spark gap waveform.

An object of the invention is to further randomize a power output waveform so as to preclude molecular resonance and attendant damage to tissue while preserving power output level required for coagulation.

An object of the invention is to produce a power output waveform comprising damped RF bursts having uniform envelopes and a controlled initial spike.

An object of the invention is to randomize the frequency of the RF signal within a burst.

An object of the invention is to provide uniform power into a wide range of load impedances which are typically encountered during electrosurgery.

An object of the invention is to provide a voice or audible annunciation of the power settings as well as error conditions such as a disconnected foot pedal and loss of aperiodicity of the RF bursts.

Other objects and advantages of the invention appear hereinafter.

Figure 1:
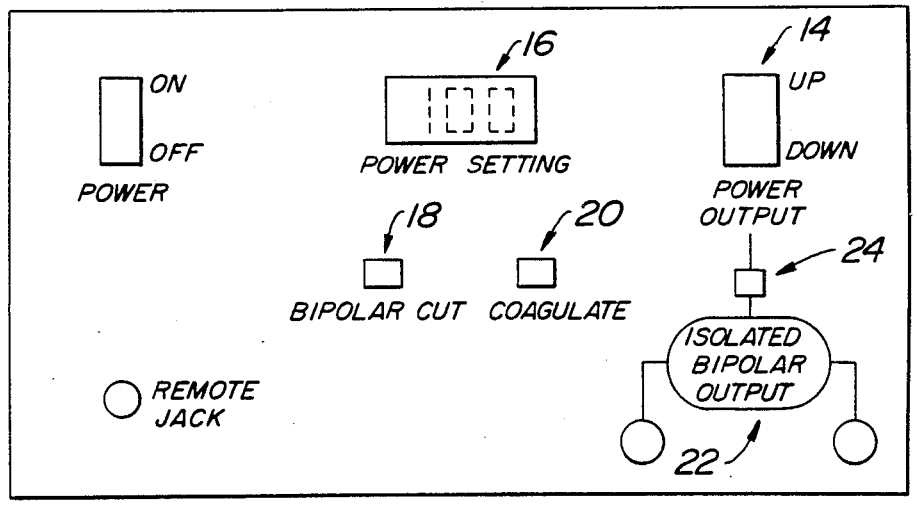
FIG. 1 is a view of the front panel of the bipolar cutter/coagulator of the present invention showing the input switches, jack connections and visual displays.

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Referring to the drawings wherein like numerals indicate like elements, there is shown in FIG. 1 a front panel 10 of the bipolar cutter/coagulator of the present invention. The front panel 10 includes a power on/off rocker switch 12 which supplies ac or line power to the cutter/coagulator when thrown to the "on" position and which disconnects the cutter/coagulator from the line when thrown to the "off" position.

The front panel 10 also includes a power up/down rocker switch 14 which is manipulated by the operator to slew the power setting for the device either up (increased power output) or down (decreased power output) as described hereinafter. If desired, a remote power up/down switch may be connected to the REMOTE jack terminal on the panel so as to enable the operator to slew the power settings at a more convenient, remote location. The power settings are visually displayed on a three-digit LED numeric display 16.

A pair of different colored LEDs 18, 20 are centrally located on the panel 10 so as to provide an indication of the mode of operation of the cutter/coagulator. In the cut mode, LED 18 is illuminated, and in the coagulate mode LED 20 is illuminated. The mode of operation, either cut or coagulate, is selected by the operator by depressing a foot pedal switch (not shown) which is connected to the back panel of the cutter/coagulator. The power output is available at the ISOLATED BIPOLAR OUTPUT jacks 22. The surgeon's forceps are connected by two wire cabling to the power output jacks. An LED 24 is provided on the front panel proximate the power output jacks. When power is being delivered to the output jacks 22, the LED 24 is illuminated.

Figure 2:
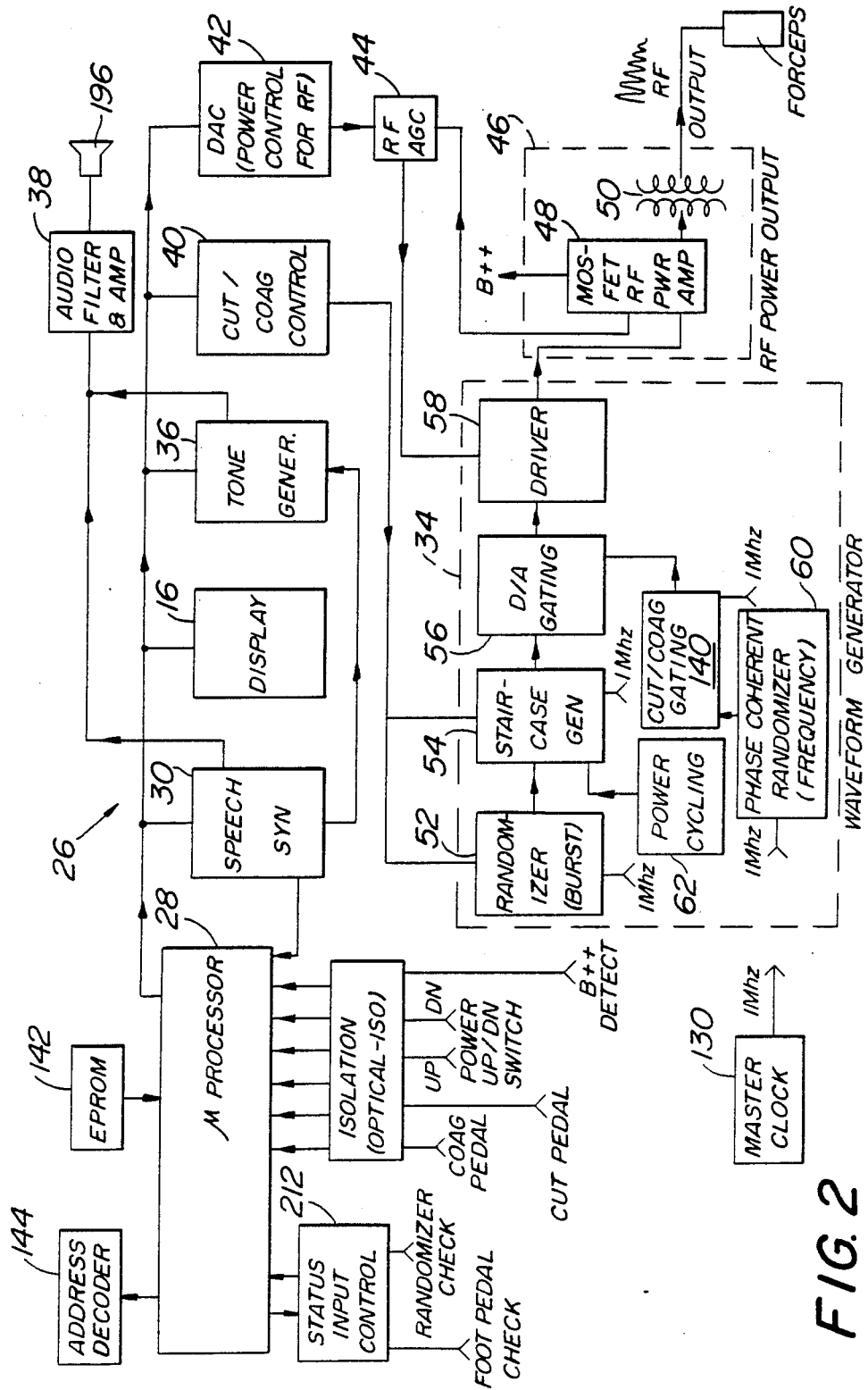
FIG. 2 is a block diagram of the invention.

Referring to FIG. 2, there is shown a block diagram of the bipolar cutter/coagulator of the present invention, designated generally as 26. The bipolar cutter/coagulator includes a programmed microprocessor 28 which receives an internal error check signal designated "Randomizer Check" and an externally generated error check signal designated "Footpedal Check" via a status input control 212. The microprocessor 28 controls a speech synthesizer 30 and the LED display 16 so as to provide voice and visual indications of the error conditions.

The microprocessor also receives Cut and Coag mode signals from a foot pedal 226, up/down Direction and Strobe signals from the power up/down switch 14, and a No B++ Detect signal from the power supply, all via an opto-isolator interface.

The microprocessor controls a waveform generator section 34 so as to produce a cut waveform used in cutting vessels or tissue or a coagulating waveform used in sealing a vessel. The microprocessor controls the speech synthesizer 30 and LED display 16 so as to provide voice and visual indications of the power output of the waveform based on the up/down Direction and Strobe signals at the isolator interface.

In response to the Cut or Coag mode signals, the microprocessor controls a tone generator 36 so as to sound a minor or major chord depending on whether the Cut mode or Coagulating mode is indicated. All voice messages, as well as the major or minor chords, are sounded by a speaker 196 which is driven by a filter and amplifier circuit 38.

The particular waveform generated by waveform generator section 34 is determined by the mode of operation, as indicated by the Cut and Coag mode signals. The waveform power is set by the up/down Direction and Strobe signals. In response to these signals, the microprocessor sets and resets a cut/coag control 40 and a digital to analog converter (DAC) 42. The cut/coag control 40 indicates to the waveform generator section 34 that either a Cut waveform or a Coag waveform is to be generated. The DAC 42 indicates the power setting to the waveform generator via an AGC loop 44. The AGC loop is connected between the wave form generator 34 and the RF power output section 46. The AGC loop maintains the power output uniform as the load swings over the range of impedances typically encountered during surgery. For example, when the forceps are immersed in a mixture of blood and saline, the load impedance may approach a "dead short" condition of 0 ohms. But in the absence of blood and saline, the load impedance may reach 5 kohms or more. The AGC loop insures that the power output at the forceps tips remains uniform despite the swing in load impedance.

The RF power output section 46 includes a MOSFET power amplifier 48 and a bipolar isolated output transformer 50. The output transformer 50 is a step down cup-core transformer which provides a very low effective output impedance, enabling the device to drive the forceps near the "dead short" condition without power loss.

The input to the RF power output section is provided by the waveform generator section 34. The waveform generator section includes a burst randomizer 52, frequency randomizer 60, cut/coag gating 140, a staircase generator 54, D/A gating 56 and a driver circuit 58. The staircase generator 54 produces a sequence of numbers of decreasing value in the form of 4-bit digital words. The envelope of each RF burst produced by the power output section 46 is determined by the sequence of 4-bit words generated by the staircase generator. The outputs of the staircase generator 54 are converted to a ramped sequence of pulses at a frequency determined by cut/coag gating circuit 140 in response to master clock 130 or frequency randomizer 60. Conversion of the staircase generator outputs to the ramped pulses is accomplished by the D/A gating circuit 56.

Each sequence of numbers of decreasing value generated by staircase generator 54 is initiated by a trigger signal generated by the burst randomizer 52. The trigger signals are generated aperiodically. The spacing between trigger signals is a pseudo random function and preferably varies between 11-51 microseconds as described hereinafter.

The spacing between damped RF bursts at the RF power output section is also pseudorandom, initiation of each RF burst being determined indirectly by a burst randomizer trigger signal. The duration of a group of bursts, however, is determined by a power cycling circuit 62. The power cycling circuit 62 also controls the duration or "dead zone" between consecutive groups of RF bursts.

RF POWER OUTPUT SECTION

Figure 18:
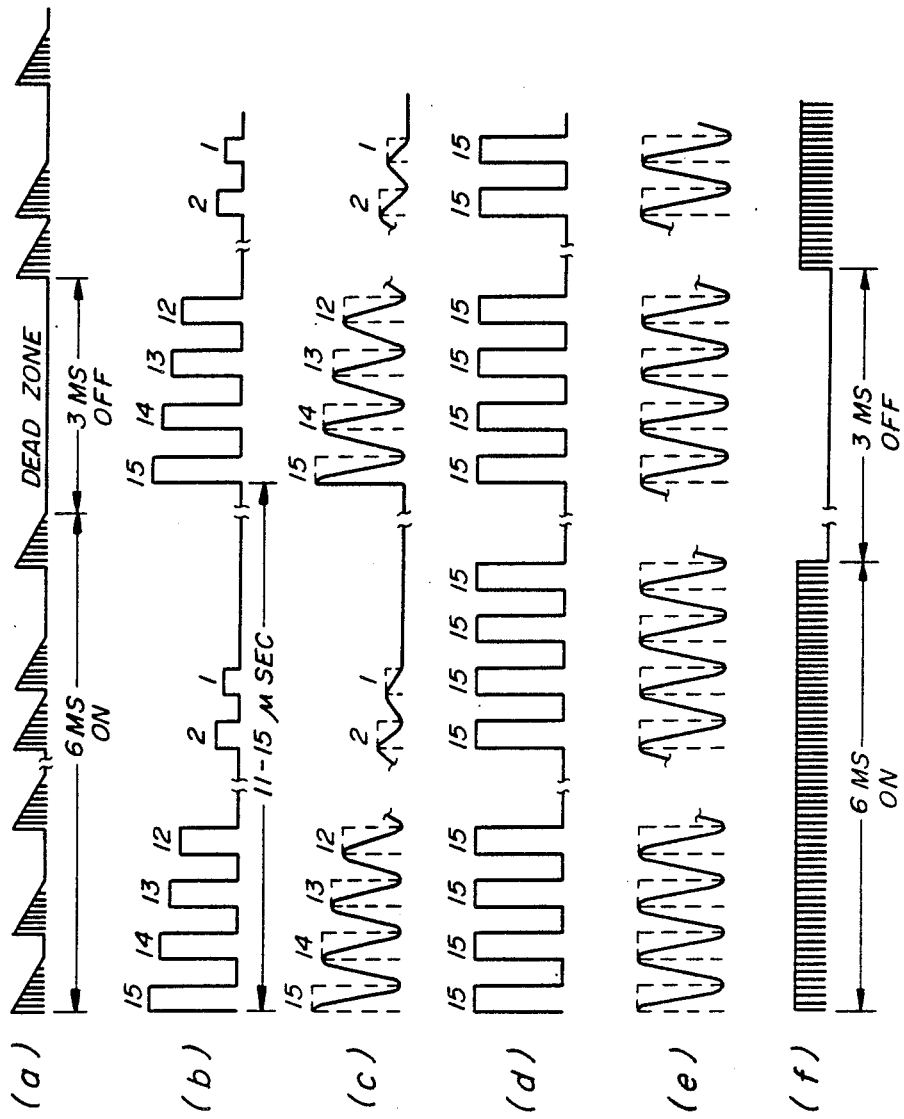
FIG. 18 is a chart of the various waveforms generated by the cutter/coagulator.

The input to the RF power output section 46 is generated by waveform generator section 34. The output of waveform generator section 34 is shown in FIG. 18(a). The output comprises regularly spaced groups of ramped bursts of pulses. The pulse bursts in each group occur in pseudorandom sequence, that is, they are generated aperiodically. Each burst is a sequence of ramped pulses as shown in FIG. 18(b). In the preferred embodiment, each pulse is ½ microsecond long.

Figure 3:
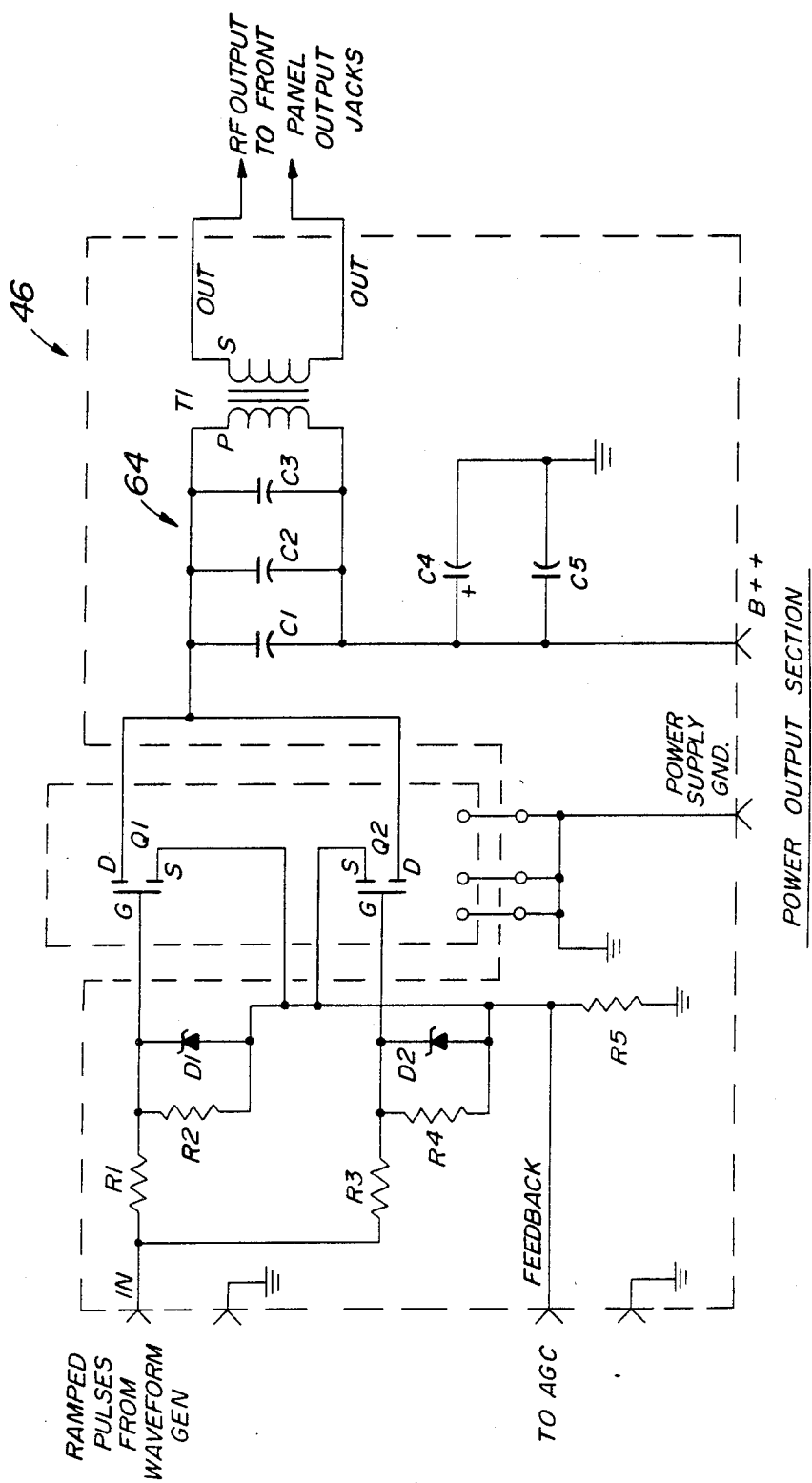
FIG. 3 is a circuit schematic of the power output section.

Referring to FIG. 3, the ramped pulses are transmitted to the IN input of the RF power output section, through resistors R1, R3, to the gates of power MOSFETs Q1, Q2. The MOSFETs Q1, Q2 are connected in parallel so as to switch on and off at the same time. It is preferred that a pair of MOSFETs be used to efficiently handle the power levels required. A pulse appearing at the IN input of the power output section switches the MOSFETs Q1, Q2 on. The drains of the MOSFETS are pulled to ground through the MOSFET sources which are connected to ground through resistor R5. In the interval between consecutive pulses, the MOSFETs Q1, Q2 are switched off so that the drains are effectively left to float.

The MOSFET drains are connected to a tank circuit 64 comprising capacitors C1, C2, C3 and the primary of output transformer T1. Capacitors C1, C2 are 3000 pf capacitors, and capacitor C3 is used for frequency trimming. When the MOSFETs are turned off, the tank circuit begins to resonate or ring. The drains of MOSFETs Q1, Q2 therefore rise in voltage. On the occurrence of the next pulse, the MOSFET drains are again pulled to ground. The MOSFET drains alternately rise and fall in voltage as shown in FIG. 18(c). A damped RF 1 Mhz sinusoidal burst is therefore impressed on the transformer T1 primary.

Preferably, the transformer is a cup-core transformer having a step down ratio of 5:3 so as to reduce the secondary output impedance. A cup-core transformer is preferred because it transfers power more efficiently than other types of transformers at 1 Mhz RF. It is preferred that the transformer primary comprise two parallel connected strands of five turn 14 gauge wire and that the transformer secondary comprise three parallel connected strands of three turn 14 gauge wire to reduce eddy current and resistive losses.

The transformer T1 secondary voltage is also a damped 1 Mhz RF sinusoidal burst. As described hereinafter, the RF burst repeats aperiodically, pseudorandom in time, based on the pseudorandom sequence of ramped pulse bursts produced by the waveform generator 34.

WAVEFORM GENERATOR SECTION

Figure 4:
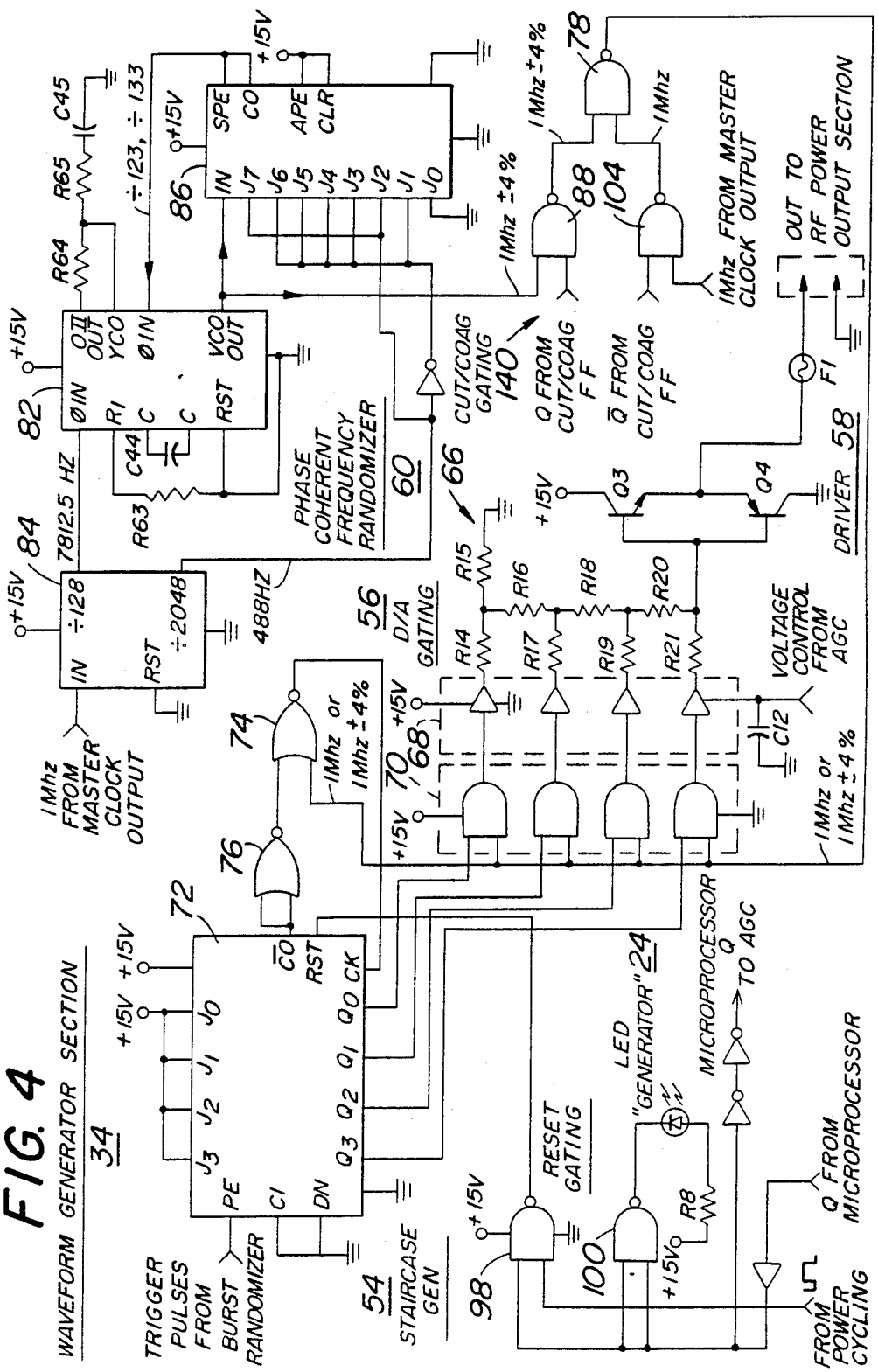
FIG. 4 is a circuit schematic of a portion of the waveform generator section.

The waveform generator section is shown in FIG. 4. The aperiodic sequence of bursts of ramped pulses is produced by the driver 58. The driver comprises a pair of complementary transistors Q3, Q4 coupled at their emitters and bases. The bases of the transistors Q3, Q4 are connected to a resistor ladder network 66 in D/A gating circuit 56.

The ladder network is a binary weighting network connected to the output of CD 4010BE buffers 68. The ladder network includes 2K resistors R14, R15, R17, R19 and R21 and 1 K resistors R16, R18, R20. Each of the buffers 68 transmits an analog voltage control signal produced by the AGC loop to the ladder network 66 when the buffer input is high. When the buffer input is low, the buffer output is also low. The states of the buffer inputs are determined by AND gates 70. The AND gates are connected to the Q0–Q3 outputs of a CD 4516BE presettable 4-bit up/down counter 72 in the staircase generator circuit 54. The Q0–Q3 outputs of counter 72 determine the relative levels of the ramped pulses generated by driver 58.

Initially, counter 72 is preset by a trigger pulse appearing at its preset enable input (PE). The trigger pulses are generated by the burst randomizer 52. The J0–J3 inputs of the counter are tied together to power supp (+15 v) so that the counter is preset to the number 15 at each trigger pulse. The counter is decremented by a clock signal at its clock (CK) input. The clock signal is generated by NOR gate 74. The clock signal frequency is either held at 1 Mhz (Cut mode) or varies between limits of 1 Mhz plus or minus 4% (Coagulate mode) as described hereinafter. Thus, the counter is decremented at a fixed rate of 1 Mhz or at a varying rate centered on 1 Mhz, depending on the mode of operation, from a count of 15 to a count of 0. When the count reaches 0, the carry output (CO) of the counter goes low. The low carry output is inverted by NOR gate 76 which disables NOR gate 74, holding the CK input of the counter low. At the next occurrence of a trigger pulse, the counter repeats the foregoing operation.

The Q0–Q3 outputs of the counter 72 define a sequence of digital words of decreasing vlaue from 15 to 0, i.e., a decreasing staircase. Each word is transmitted by AND gates 70 to buffers 68 in response to the 1 Mhz (Cut mode) or 1 Mhz plus or minus 4% (Coagulate mode) signal appearing at the input of NOR gate 74. It should be appreciated that the digital words are produced at the Q0–Q3 outputs of counter 72 at the 1 Mhz or 1 Mhz plus or 4% rate and are synchronously gated at the same rate to the buffers 68.

Each digital word at the Q0–Q3 outputs of counter 72 represents a nominal pulse level. The actual level of the pulse is determined by the level of the AGC voltage control signal as described hereinafter.

FREQUENCY RANDOMIZER

The frequency of the ramped pulses inside each burst is varied in the Coagulate mode only by the phase coherent frequency randomizer circuit 60. The frequency randomizer circuit 60 includes a CD 4046BE phased locked loop (PLL) 82. The PLL is connected to resistors R63, R64, R65 and capacitors C44, C45 having the following values:

| R63 | R64 | R65 | C44 | C45 |
|---|---|---|---|---|
| 4.7K | 10K | 2.2K | 120 pf | .01 mf |

One phase input (φIN1) to the PLL is a 7812.5 hz signal provided at the divide by 128 output of a CD 4040BE 12 stage ripple counter 84 which is clocked at a 1 Mhz master clock rate. The other phase input (φIN2) of the PLL 82 is generated by a CD 40103BE presettable 8-bit binary down counter 86. The down counter 86 is alternately preset at 488 hz to complementary digital numbers at its J1–J7 inputs so as to cause the counter to divide the frequency of the PLL VCO out signal alternately between factors of 123 and 133. The frequency of the VCO out signal therefore sweeps alternately between 0.96 Mhz and 1.04 Mhz at a 488 hz rate. The 488 hz signal therefore controls the rate at which the frequency of the VCO out signal is swept. Both the 7812.5 hz and 488 hz inputs to the PLL 82 are derived from the 1 Mhz master clock signal. Accordingly, the VCO output of the PLL is in phase coherence with the 1 Mhz master clock signal although it gradually varies between plus or minus 4% from the 1 Mhz frequency in the Coagulate mode.

The frequency swept 1 Mhz VCO output is transmitted to NAND gate 88 in cut/coag gating circuit 140. When the NAND gate is enabled by the Q output of the cut/coag flip-flop, described hereinafter, the NAND gate transmits the VCO output to AND gates 70 and NOR gate 74 via NAND gate 78. Accordingly, the ramped pulses generated by the gating circuit 56 and driver 58 are generated in phase coherence with the 1 Mhz master clock signal although the frequency of the pulses sweeps between 1.04 Mhz and 0.96 Mhz. By sweeping the frequency of the ramped pulses within the bursts during coagulation, the harmful effects introduced by regularly occuring waveforms, namely molecular resonance and attendant inadvertent cutting or perforation of tissue, are avoided.

POWER CYCLING AND RESET GATING

During coagulation, the swept frequency RF bursts recur aperiodically over preset on and off times as shown in FIG. 18(a). For example, a sequence of aperiodic, frequency swept bursts is generated during 6 milliseconds followed by a deadzone of 3 milliseconds. During the next 6 milliseconds, another sequence of bursts is generated, followed by another 3 millisecond dead zone. The duration of a sequence of bursts, and the duration of a dead zone, is determined by the power cycling circuit 62. See FIG. 5.

The power cycling circuit 62 includes a free-running oscillator such as a CA555CE timer 90. The timer is connected to resistors R9, R10 and capacitor C8 so as to produce a pulse waveform having a 9 millisecond period and a duty cycle characterized by a 6 millisecond on time and a 3 millisecond off time when it free-runs. The preferred values of the resistors and capacitors are:

| R9 | R10 | C8 |
|---|---|---|
| 392K | 82K | .022 mf |

In the Coagulate mode, the $\overline{Q}$ output of cut/coag flipflop 40 is low. The $\overline{Q}$ output is transmitted by a CD 40109 low to high voltage interface driver 92 to NAND gate 94. The NAND gate 94 produces a high output, reverse biasing the diode CR3 so that the timer 90 free-runs producing the desired power cycling waveform. In the cut mode, the $\overline{Q}$ output of cut/coag flipflop 40 is high, resulting in a low NAND gate 94 output. This forward biases diode CR3, causing the timer 90 output to stay high. The output of the timer 90 is connected to a reset gating circuit 96 in the wave form generator section. See FIG. 4.

During the 6 millisecond on time of the power cycling waveform, NAND gate 98 (reset gating circuit) produces a low output. Accordingly, the staircase generator 54, D/A gating 56, and driver 58 operate as previously described, producing an aperiodic sequence of bursts of ramped pulses during the 6 millisecond interval. The RF power output section therefore produces an aperiodic sequence of bursts of damped RF during the 6 millisecond interval. When the power cycling circuit output is low, during the 3 millisecond dead zones, the output of NAND gate 98 goes high, resetting the counter 72 so that the outputs Q0-Q3 stay low. Thus, during a 3 millisecond dead zone no pulse bursts are produced the waveform generator section or the RF power output section.

The power cycling output repeatedly releases and resets the counter 72 in the Coagulate mode so as to produce 6 millisecond long aperiodic sequences of bursts of ramped pulses at the waveform generator output, separated by 3 millisecond long dead zones. During this time, a NAND gate 100 (FIG. 4) clamps the cathode of "generator" LED 24 low so that the LED provides a visual indication that the cutter/coagulator is operating.

As indicated above, the power cycling and reset gating circuits operate counter 72 to periodically produce aperiodic sequences of bursts of ramped pulses in the Coagulate mode. In the Cut mode, however, the $\overline{Q}$ output of the cut/coag flipflop 40 is high, so that the power cycling and reset gating circuits do not reset the up/down counter 72. As described in further detail hereinafter, this permits the counter 72 to be rapidly and repetitively preset so that the Q0-Q3 outputs of the counter remain at the preset number 15 without being counted down. In addition, since the $\overline{Q}$ output of the cut/coag flipflop 40 is high in the cut mode, NAND gate 104 in the cut/coag gating circuit 140 (FIG. 4) passes the 1 Mhz master clock pulses to AND gates 70 via NAND gate 78. The 1 Mhz pulses at the AND gate 70 inputs chop the Q0-Q3 outputs of counter 72, which remain preset, to produce a steady 1 Mhz undamped pulse stream at the output of driver 58. See FIG. 18(d). Thus, in the Cut mode the output of driver 58 is a continuous 1 Mhz pulse stream without any damping, frequency sweep, or dead zones. Accordingly, the power output section generates a continuous, undamped 1 Mhz RF burst as shown in FIG. 18(f).

BURST RANDOMIZER CIRCUIT

In both the Cut and Coagulate modes, the counter 72 is operated in response to the trigger pulses produced by the burst randomizer circuit 52. The burst randomizer circuit is shown in detail in FIG. 5. When the $\overline{Q}$ output of the cut/coag flip-flop 40 is low, indicating operation in the Coagulate mode, the burst randomizer circuit generates a pseudorandom sequence of trigger pulses. If the $\overline{Q}$ output is high, indicating operation in the Cut mode, the burst randomizer generates a steady, non-random sequence of 1 Mhz pulses. Each trigger pulse presets counter 72 (FIG. 4) to the number 15 as previously described. In the Coagulate mode, the trigger pulses are spaced far enough apart to decrement counter 72, but in the Cut mode they are not.

The burst randomizer circuit 52 is actually a digital pseudo-random pulse generator which provides the aperiodicity or "randomness" of a spark gap burst without the undesirable features of the spark gap. The burst randomizer circuit includes a CD 4006BE 18 bit shift register 106. The data input (DIN) to the shift register 106 is determined by exclusive OR gate 108 and seed circuit 110. Seed circuit 110 includes a NOR gate 112 and inverters 114, 116. NOR gate 112 and inverter 114 perform a logic OR function. The input to inverter 116 is connected to a RC charging circuit 118 comprising a 10 microfarad capacitor C43 and a 22K resistor R62. When power is initially turned on, capacitor C43 charges towards the +15 v supply voltage. Resistor R62 and capacitor C43 are chosen to provide an approximate 0.25 second delay or charge up interval during which the input to inverter 116 is held low. The DIN input to the shift register 106 is therefore maintained at a high logic level or binary 1 during the charge up interval. A NOR gate 119 transmits the 1 Mhz master clock pulses to the clock input (CK) of the shift register. The 1 Mhz clock pulses therefore shift a series of binary 1's into the shift register. Thus, the seed circuit 110 insures that the shift register 106 is seeded with binary 1's during the charge up interval.

Once the capacitor C43 has charged to a high logic level, the inverter 116 output goes low. The exclusive OR gate 108 is connected to bits 17 and 18 of the shift register 106 so that both inputs of the gate are high at this time, producing a low logic level or binary 0 at the shift register DIN input. The 1 Mhz clock pulses therefore begin to shift binary 0's into the register 106.

The 13th, 17th and 18th bits of register 106 provide a pseudorandom sequence of binary numbers having decimal values M=0-7. These numbers are used to provide the pseudorandom spacing between the trigger pulses. Each trigger pulse triggers a burst of ramped analog pulses at the waveform generator section output (FIG. 4) as previously described. It is desirable to pack the ramped bursts as closely together as possible within the 6 millisecond on time of the power cycling waveform so as to maximize the power at the waveform generator output. If the trigger pulses are spaced too closely together, however, they will maintain the counter 72 (FIG. 4) in the preset condition and the waveform generator output pulses will not be ramped. The resulting waveform generator output would be as shown in FIG. 18(f). In effect, the waveform generator would produce a continuous 6 millisecond long stream of uniform amplitude pulses every 3 milliseconds, similar to a cut waveform, but in the Coagulate mode. This condition would occur if the J4, J5 and J6 inputs to the divide by 10N+1 circuit 120 were permitted to reach a decimal value N=0 corresponding to the value M=0 of the shift register 106 outputs.

On the other hand, if the trigger pulses are spaced too far apart, the power level of the waveform generator pulse bursts would be objectionaly low. This condition would occur if the J4, J5 and J6 inputs of the divide by 10N+1 circuit 120 were permitted to reach a decimal value N=6 or 7 corresponding to the values M=6, 7 of the shift register 106 outputs.

To prevent the J4, J5 and J6 inputs of the divide by 10N+1 circuit 120 from assuming an objectionably low decimal value (N=0) or an objectionably high value (N=6, 7), the 13th, 17th and 18th bits of the shift register 106 are converted to a BCD number which varies between the decimal values N=1-5 only. The conversion is accomplished by a CD 4028BE BCD to decimal decoder 122 coupled to a CD 4532BE 8-bit priority encoder 124 by exclusive OR (EXOR) circuit 126. The EXOR circuit 126 maps decimal 0 and 6 at the decoder 122 output to decimal 2 at the priority encoder 124 input, and decimal 1, 2 or 7 at the decoder 122 output to decimal 1 at the priority encoder 124 input. The outputs Q0-Q2 of the priority encoder 124, therefore, produce a pseudorandom sequence of BCD numbers having the decimal values N=1-5. These numbers appear at the J4-J6, inputs of the divide by 10N+1 circuit 120.

The divide by 10N+1 circuit 120 divides the 1 Mhz master clock frequency by the factor $10 \times (N=1)+1=11$ to $10 \times (N=5)+1=51$ in response to the J4-J6 inputs. Thus, circuit 120 counts down at the 1 Mhz rate from the number N at the J4-J6 inputs to 0. When the count reaches 0, the carry output (C0) of circuit 120 goes low, enabling NOR gate 119 to pass a master clock pulse to the preset enable (PE) input of the up/down counter 72 (FIG. 4). This is the trigger pulse. The trigger pulse is also fed to the CK input of shift register 106 to clock the shift register and produce a new number N at the J4-J6 inputs of the divide 10N+1 circuit 120. The next trigger pulse appears at the output of NOR gate 119 10N+1 microseconds later.

In sum, in the Coagulate mode, the spacing between consecutive trigger pulses, namely 10N+1 microseconds, is a pseudorandom function because the number N varies between 1-5 in a pseudorandom sequence as determined by the 13th, 17th, and 18th bits of shift register 106.

In the Cut mode, the trigger pulses ar not pseudo random, and they occur regularly at the 1 Mhz rate. Thus, in the Cut mode, the Q output of the cut/coag flipflop 40 is high. The Q output is passed by driver 92 to inverter 128 which clamps the enable input (EI) of priority encoder 124 low, thereby inhibiting operation of the priority encoder. The Q0-Q2 outputs of the priority encoder therefore remain low, corresponding to a BCD number having a decimal equivalent N=0. The divide by 10N+1 circuit 120 therefore divides the 1 Mhz master clock pulse frequency by $10 \times (N=0)+1=1$. In other words, the 1 Mhz pulses are passed directly to NOR gate 119. As a result, both inputs of NOR gate 120 carry the 1 Mhz pulse train, so that the trigger pulses produced by the NOR gate are the 1 Mhz master clock pulses shifted 180°.

The 1 Mhz trigger pulses maintain the counter 72 (FIG. 4) preset to the number 15 in the Cut mode because they occur at the same rate as the clock pulses at the CK input of the counter. The counter 72, then, cannot be counted down. The gating circuit 56 (FIG. 4) chops the Q0-Q3 outputs of the counter 72 at the 1 Mhz frequency. Since the Q0-Q3 outputs remain preset at the number 15, the output of the driver circuit 58 is a 1 Mhz pulse train of uniform amplitude.

MASTER CLOCK CIRCUIT

Figure 6:
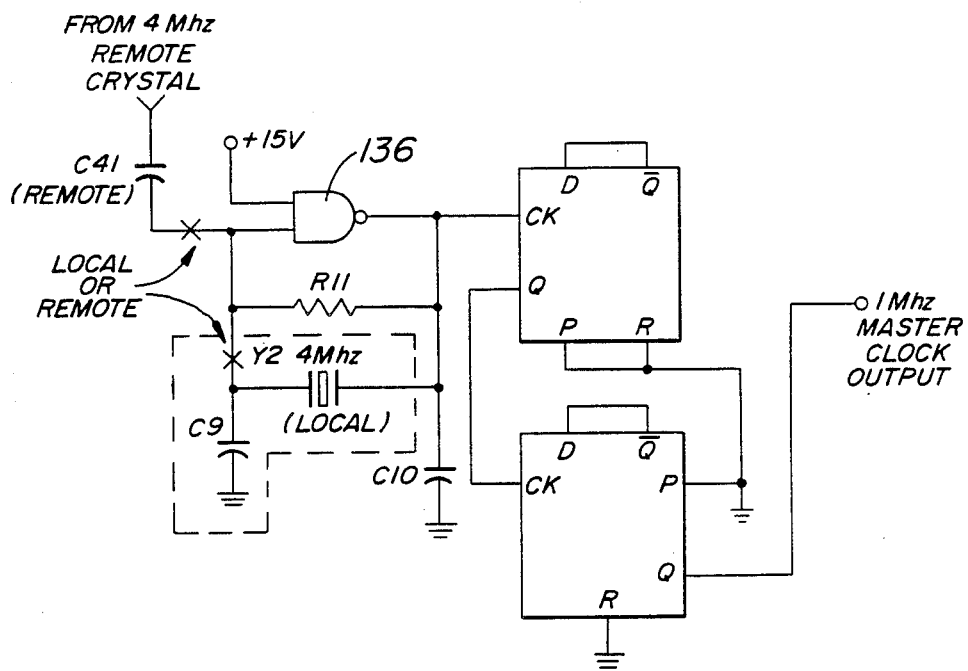
FIG. 6 is a circuit schematic of the master clock.

The 1 Mhz master clock pulses are generated by a master clock circuit 130. See FIG. 6. The master clock circuit is connected to the burst randomizer 52, staircase generator 54 and phase coherent frequency randomizer 60 as previously described. The output of the master clock circuit is a 1 Mhz square wave derived from a 4 Mhz crystal Y2 by a pair of flipflops 132, 134. The flip flops are connected so as to divide the 4 Mhz crystal output by a factor of 4.

The master clock circuit 130 may be operated in a local or a remote mode. In the local mode, the crystal Y2 is connected across the resistor R11 and capacitor C41 is disconnected from the NAND gate 136 input. In the remote mode, crystal Y2 is disconnected from resistor R11, and capacitor C41 is connected to the NAND gate 136 input. A remote 4 Mhz crystal circuit 138 in the speech synthesizer 30 (FIG. 10) is employed as the clock reference. The crystal circuit 138 is ac coupled to the NAND gate 136 input by capacitor C41.

AUTOMATIC GAIN CONTROL (AGC)

Figure 7:
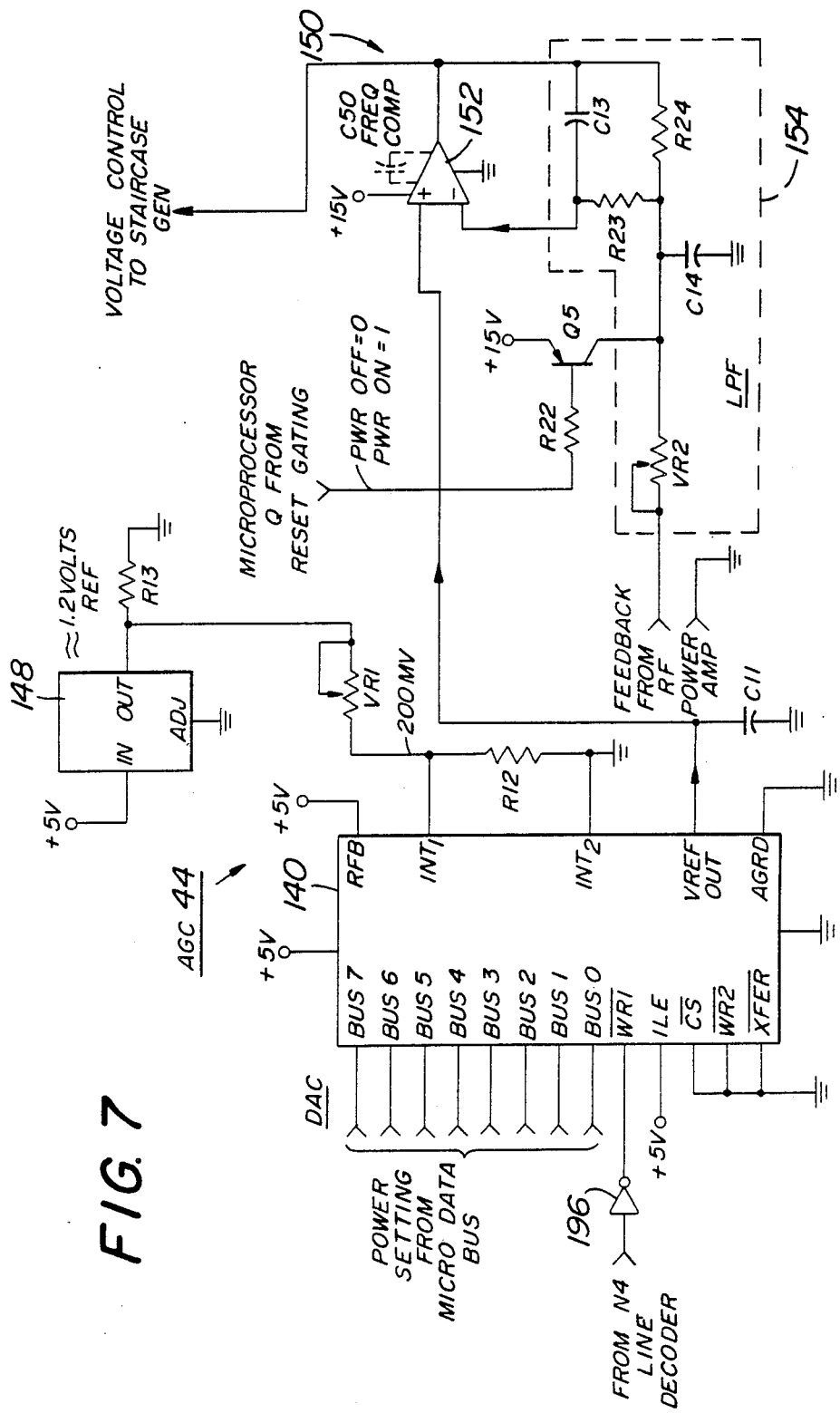
FIG. 7 is a circuit schematic of the DAC and automatic gain control (AGC) loop.

The ACG loop ensures that the power output section delivers uniform power over the full range of load impedances. The AGC circuit 44 is shown in FIG. 7.

The circuit produces the analog voltage control signal which controls the output of buffers 68 in the waveform generator section (FIG. 4). As previously indicated, the buffers 68 transmit the analog voltage control signal from the AGC to the resistors R14, R17, R19, and R21 of the resistor ladder network 66. The relative levels of the pulses produced by the D/A gating circuit 56 are set by the counter 72 outputs. The absolute levels are set by the level of the voltage control signal. The level of the voltage control signal is based on the power setting.

The power setting is determined by the power up/-down rocker switch 14 at the front panel 10 (FIG. 1). The microprocessor 28 (FIG. 2) generates an 8-bit digital word representative of the power setting based on the state of the power up/down switch. The digital word is fed to the BUS 0-7 data inputs of a DAC0832LCN digital to analog converter (DAC) 140. The digital word is retrieved by the microprocessor from a look-up table in a MM2716Q 2K EPROM 142 which also contains the microprocessor program. The microprocessor 28 is a CDP 1802CE chip which addresses the EPROM 142 via a CD4042AE quad clocked D latch address decoder 144. The EPROM 142 is addressed under control of the microprocessor 28 in response to the power up/down Direction and Strobe signals (FIG. 13) as described hereinafter. Thus, the Direction and Strobe signals are utilized by the microprocessor to generate the 8-bit power setting word at the input of DAC 140 (FIG. 7).

The power up/down switch 14 is a three-position switch: up, neutral and down. See FIG. 13. The Strobe signal is connected to the external flag input EF4 of microprocessor 28. When switch 14 is depressed to the up or the down position, the Strobe signal goes low. The microprocessor 28 detects this condition and enters an UP/DOWN routine described hereinafter. In the UP/DOWN routine, the microprocessor scans its BUS 0 input. The BUS 0 input is connected to the output of a CD4016BE quad transmission gate 146. See FIG. 12. The input to the transmission gate is the Direction signal from the switch interface (FIG. 13). If the Direction signal is high, it indicates that the switch is in the power up position. If it is low, it indicates that the switch is in the power down position. In response, the microprocessor addresses the EPROM 142 via address decoder 144 so as to retrieve from the EPROM the next higher (power up) or lower (power down) power setting. The power setting is transmitted to the BUS 0-7 inputs of the AGC DAC 140 (FIG. 7).

The DAC 140 is connected to a LM317MP adjustable voltage regulator 148 which provides a 1.2 volt reference signal at its output based on a +5 volt power supply signal. The reference signal is connected to a 2K 10 turn potentiometer VR1 which is set so as to provide a 200 millivolt reference signal across the INT 1 and INT 2 inputs of DAC 140. Accordingly, the voltage reference (VREF) output of the DAC varies between 0-200 millivolts, depending on the power setting at the BUS 0-7 inputs.

The VREF output is transmitted to the non-inverting input of an analog comparator and low pass filter 150 having a cutoff of approximately 4 Hz. The analog comparator and low pass filter 150 comprises a CA3130E operational amplifier 152 and a 4Hz cutoff low pass filter 154. The low pass filter includes a 50K 10 turn pot VR2, resistors R23 and R24, and capacitors C13 and C14. The values of the resistors and capacitors are given below.

| R23 | R24 | C13 | C14 |
|---|---|---|---|
| 40.2K | 3.3 M | .01 uf | .1 uf |

The inverting input of operational amplifier 152 is connected via the low pass filter 154 to feedback resistor R5 in the power output section 46. See FIG. 3. Voltage across feedback resistor R5 is proportional to current flow through the MOSFET sources and constitutes the feedback voltage to the AGC loop. The difference between the voltages at the inverting and non-inverting inputs of the operational amplifier 152 represent the gain control error signal. The greater the error signal, the greater the level of the voltage control signal at the output of operational amplifier 152.

The purpose of the 4 Hz cutoff low pass filter 154 is to prevent surges in the AGC loop during the 3 millisecond off time (dead zones) of the power cycling waveform. During the 3 millisecond off time, no waveform is generated by the waveform generator section. The RF output of the power output section 46 therefore drops to zero, as does the feedback signal from resistor R5. The sudden drop in the feedback signal would result in a surge in the error signal and, therefore, the voltage control output of the AGC loop. Since the 3 millisecond off times of the power cycling waveform occur every 9 milliseconds, or at approximately 110 Hz, the voltage control output would surge at approximately 110 Hz. The result would be an uneven power output at the secondary of transformer T1 in the power output section (FIG. 3). The 4 Hz cutoff low pass filter 154 rejects the 110 Hz dips in the feedback signal so as to avoid corresponding surges in the voltage control output of the AGC loop. As a result, the RF power output signal is smooth, and surging or arcing at the forceps is avoided.

The AGC loop 44 also compensates for thermal drift of the circuit elements including the power MOSFETs in power output section 46, differences in the gain characteristics between the MOSFETs, differences in tolerance between resistors in the resistor ladder network 66, and differences between the drive characteristics of driver transistors Q3, Q4 in waveform generator section 34 (FIG. 4).

Figure 8A:
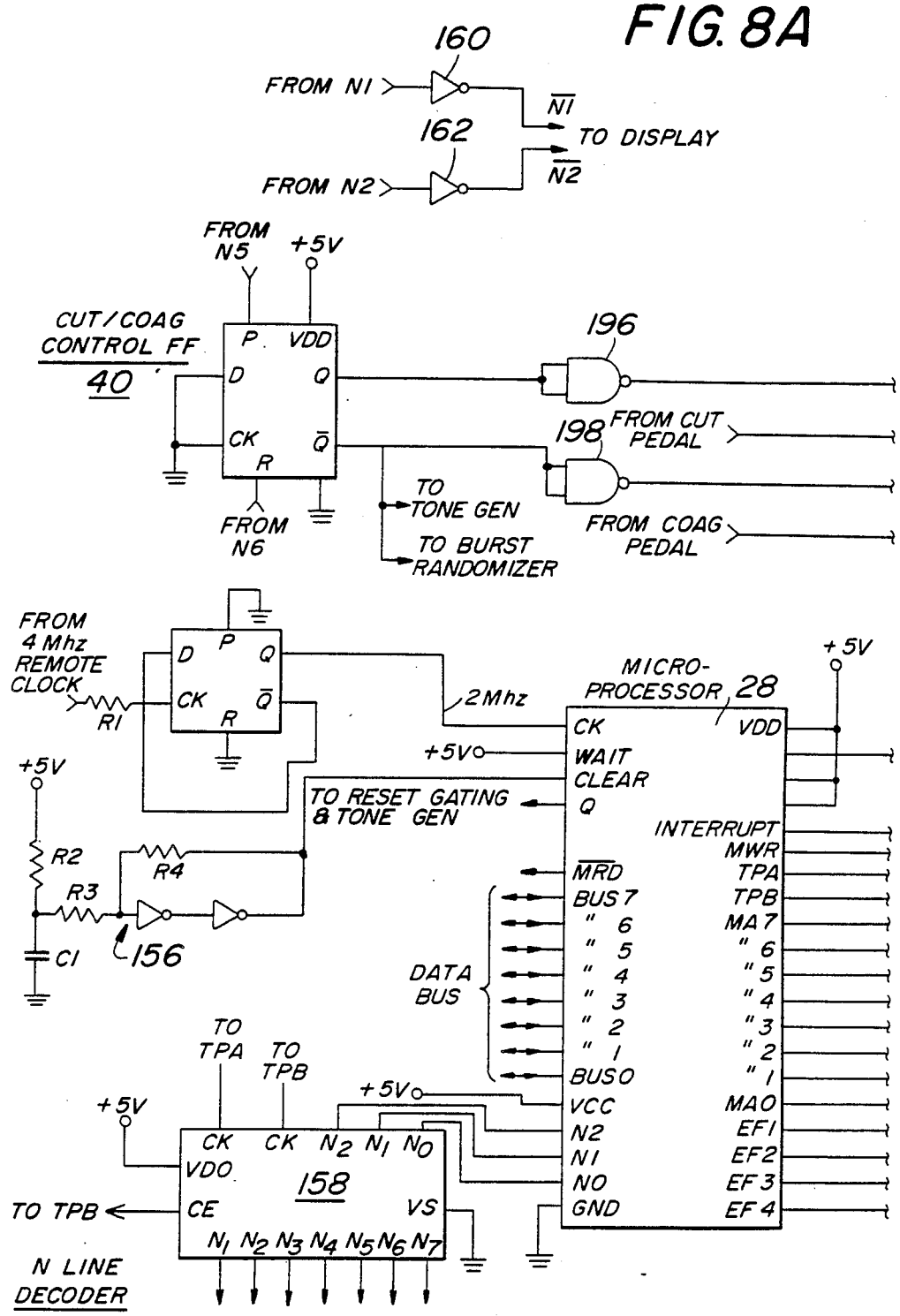
FIG. 8A and 8B comprise a schematic of the microprocessor memory address and control circuitry.
Figure 8B:
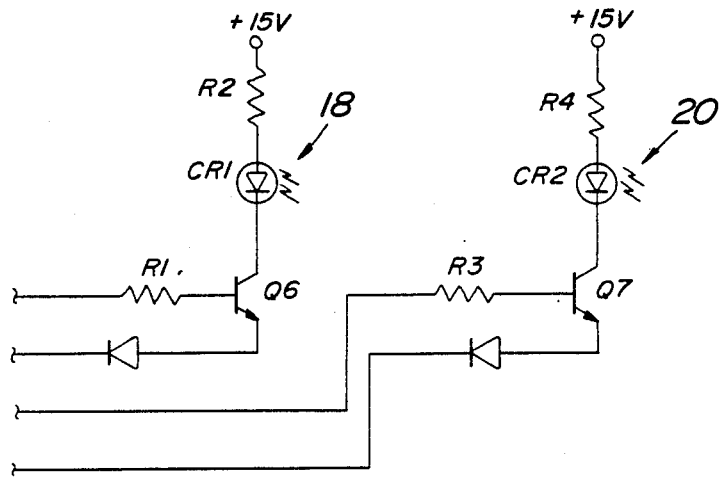
Figure 8B:
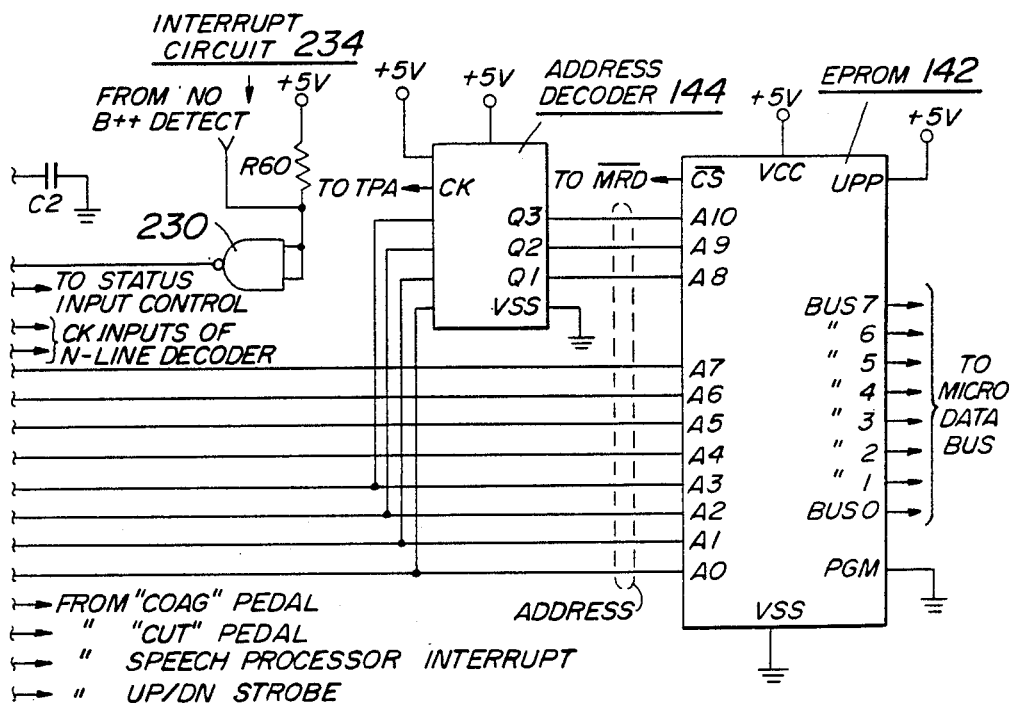

Further, the AGC loop 44 includes a transistor Q5 which smooths the initial or attack portion of an RF burst envelope when a power setting is first generated at the DAC inputs. The transistor Q5 is coupled to the low pass filter 154 between potentiometer VR2 and capacitor C14. The base of the transistor Q5 is connected to the Q output of the microprocessor (FIG. 8). The Q output of the microprocessor is switched high or low as a software function described hereinafter. The Q output of the microprocessor is switched low before the microprocessor first generates the power setting for the DAC 140. Accordingly, transistor Q5 is turned on and capacitor C14 charges to +15 v. The voltage control output of amplifier 152 is therefore clamped to ground.

When a power setting is first generated for the DAC, the Q output of the microprocessor is switched high, turning transistor Q5 off. The DAC 140 generates a VREF output signal at the noninverting input of the operational amplifier 152 based on the power setting. The difference between the VREF signal and the voltage at capacitor C14 constitutes a finite error signal but the voltage control output of amplifier 152 is clamped to ground by the residual voltage on capacitor C14. Capacitor C14 must first discharge to the voltage at the output of operational amplifier 152, which is zero, before the voltage control output of operational amplifier 152 can start to rise. Thereafter, the voltage control output of the operational amplifier rises gradually to reduce the error signal. The result is a gradual, controlled rise in the envelope of the RF burst at the power output section as opposed to an abrupt transition which would occur if the capacitor C14 were discharged before the DAC power setting was generated. An abrupt rise in the burst envelope can result in damage to tissue as well as to circuit components.

N-LINE DECODER

The microprocessor 28 is connected to a CDP1853CE N-line decoder 158 which can be used for selecting up to seven functions. See FIG. 8. The N1-N7 outputs of the decoder control the display 16, speech synthesizer 30, the cut/coag flip-flop 40, the write control for the AGC DAC 140, and the status input control 212.

$\overline{N1}$ $\overline{N2}$/LED DISPLAY

Figure 9:
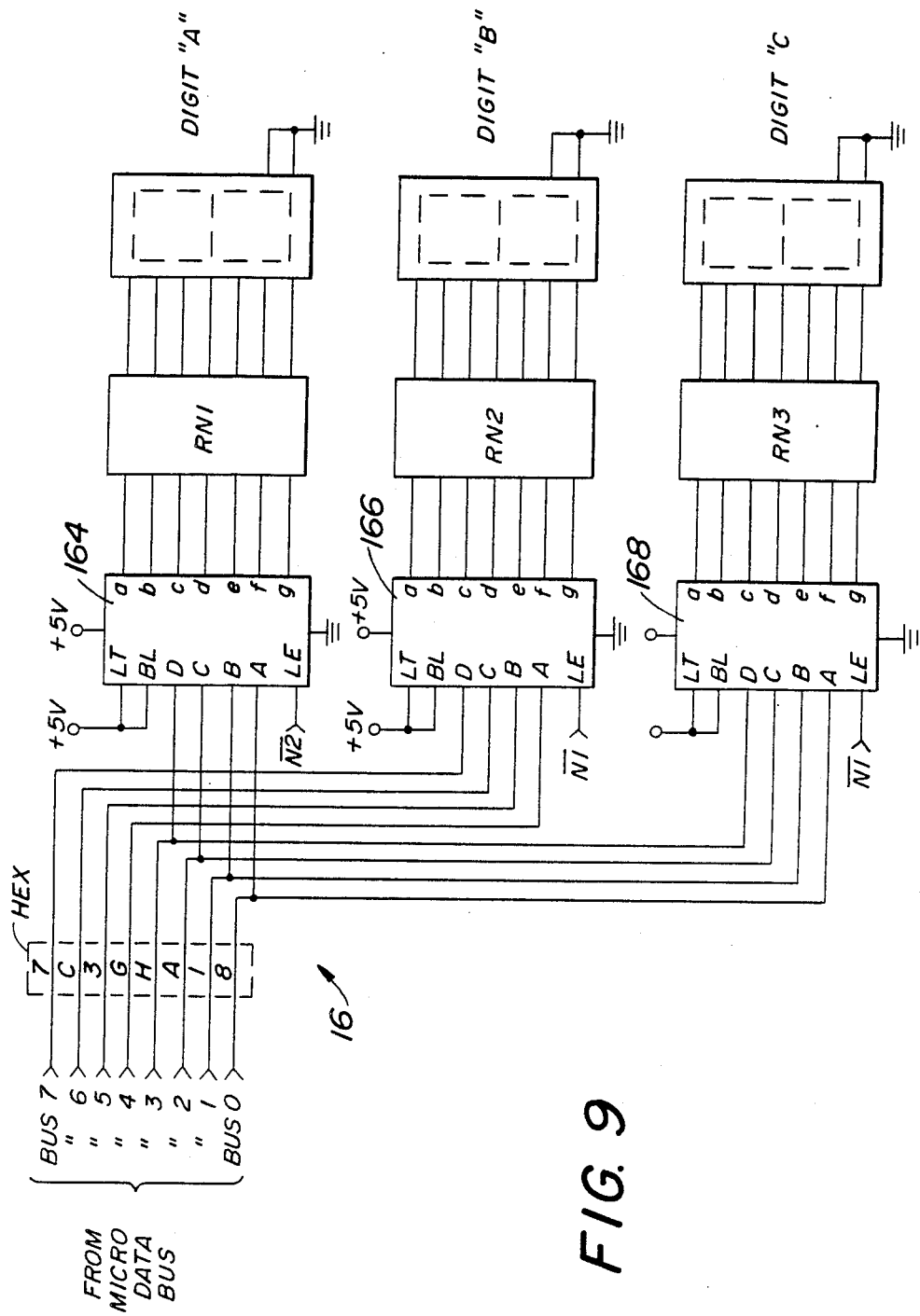
FIG. 9 is a circuit schematic of the LED numeric display.

The N1 and N2 outputs of the N-line decoder 158 control the LED numeric display 16. See FIG. 9. The N1 and N2 outputs are inverted by inverters 160, 162 to form the complements $\overline{N1}$, $\overline{N2}$ respectively. The $\overline{N1}$, $\overline{N2}$ signals control the latch enable inputs of CD451BE BCD to 7 segment latch decoder drivers 164, 166 and 168. The A-D inputs to the decoders 164, 166, 168 are taken off the BUS 0-7 lines of the microprocessor data bus. The BUS 0-7 lines carry the power settings and error messages, described hereinafter, in hexadecimal. The power settings and messages are retrieved from the EPROM 142 look-up table. The decoder driver outputs drive the LED display digits A, B, C in conventional fashion via 220 ohm resistor networks RN1, RN2, RN3.

While the power up/down switch is in the up or down position, the microprocessor generates successive power settings on the data bus, based on data in the EPROM look-up table, and displays the same on the LED display digits A-C. When the power up/down switch is released to the neutral position, the microprocessor holds the power setting on the data bus so that the display digits A-C provide a visual indication of the selected power setting. If an error condition is detected, the microprocessor generates a numerical error message on the data bus and displays the message on the LED display.

N3/SPEECH SYNTHESIZER

The N3 output of the N-line decoder 158 controls the speech synthesizer 30. See FIG. 10. The speech synthesizer 30 is a commerically available circuit. The circuit includes a MM54104 DIGITALKER processor 170 and a 4K MM2732 EPROM 172. The EPROM 172 contains digitized speech information used by the processor 170. The EPROM contains approximately 25 words, including the words "Cutting", each of the power settings, "Footpedal", "Recycle Power" and "Internal Fuse".

The N3 output is inverted by an inverter 174 to control the write control ($\overline{WR}$) input of the processor 170. When the N3 output is high, the $\overline{WR}$ input is low, and the processor 170 writes the digital information on the microprocessor data bus into the processor 170 BUS 0–7 inputs. The processor 170 then addresses the EPROM 172 on lines A0–11. The EPROM sends back to the processor 170 the digitized speech data called for by the BUS 0–7 inputs to the processor. The output of the processor 170 is an analog voice signal which is transmitted to the voice filter and amplifier circuit 38.

Figure 12:
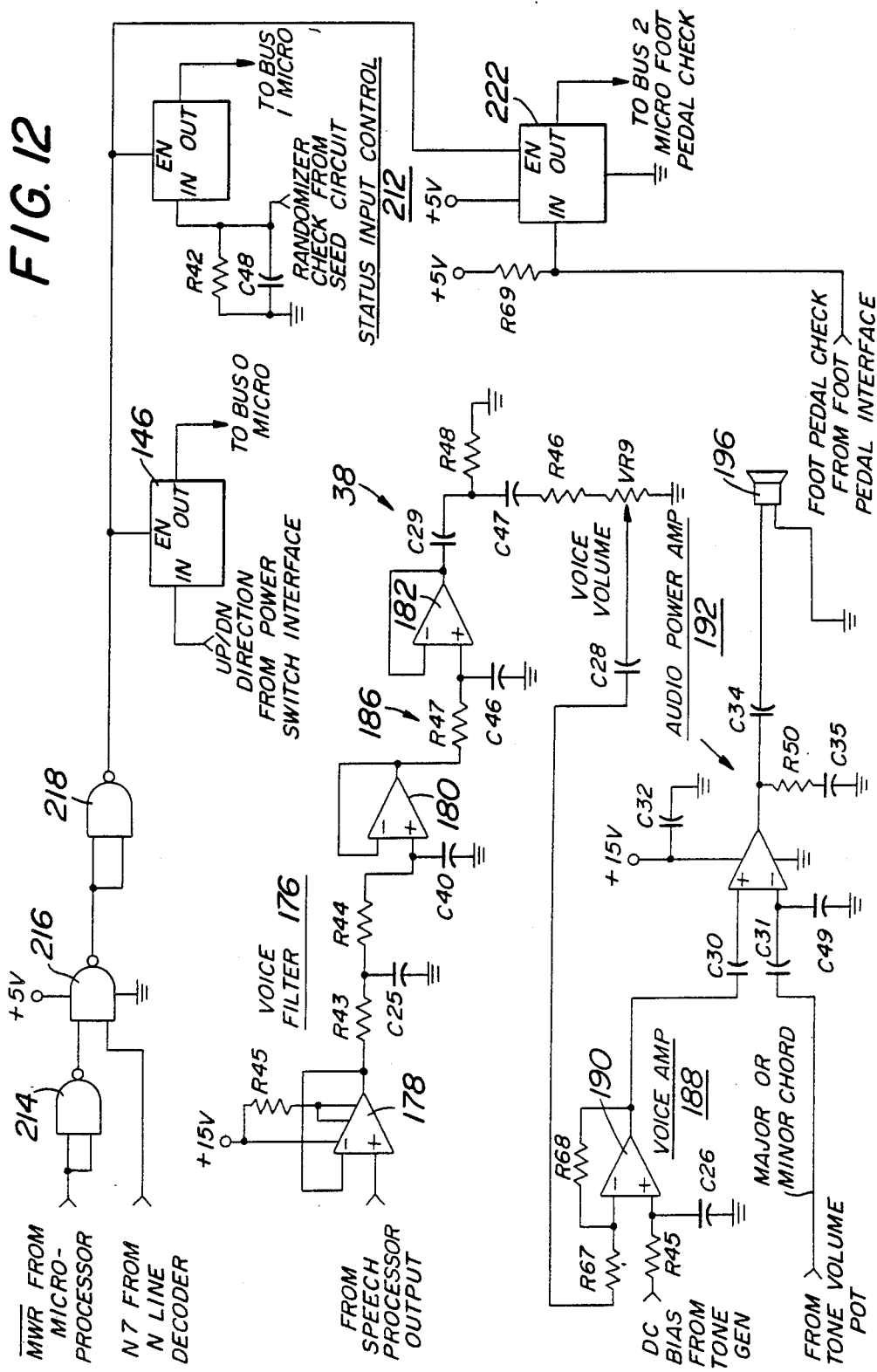
FIG. 12 is a circuit schematic of the voice filter and amplifier and the status input control.
Figure 13:
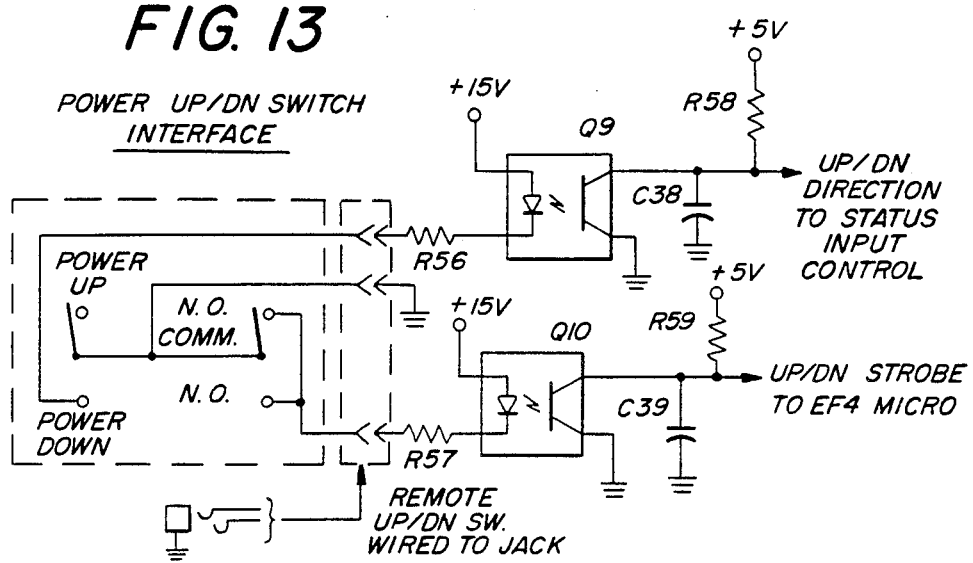
FIG. 13 is a circuit schematic of the power up/down switch interface.

The voice filter and amplifier circuit 38 is shown in FIG. 12. The circuit includes a voice filter circuit 176 comprising LM346N quad operational amplifiers 178, 180 and 182 connected as unity gain buffer drivers. Amplifiers 178, 180 are coupled by a low pass filter 184 comprising resistors R43, R44 and capacitors C25, C40 having the following values:

| R43  | R44 | C25  | C40   |
|------|-----|------|-------|
| 2.7K | 27K | .1 uf | .01 uf |

Figure 10:
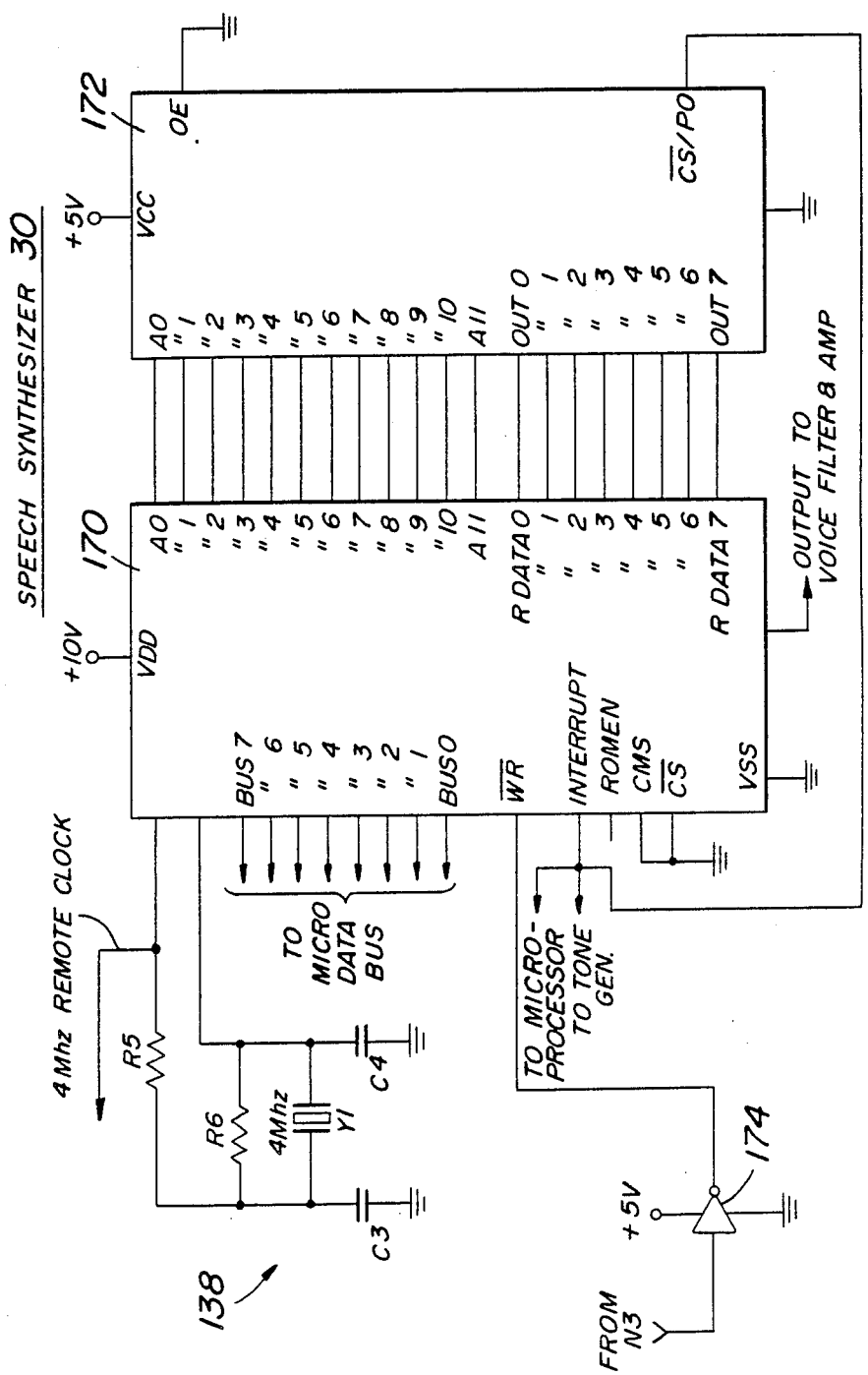
FIG. 10 is a circuit schematic of the speech synthesizer.

Amplifiers 180, 182 are coupled by a RC circuit 186 comprising a 6.5K resistor R47 and a 0.1 uf capacitor C46. The output of amplifier 182 is ac coupled to a 50K voice volume potentiometer VR9. The output of the voice volume control potentiometer VR9 is ac coupled to a voice amplifier 188 comprising operational amplifier 190. The gain of the operational amplifier is set by the ratio of resistors R68/R67. In the preferred embodiment, resistor R68 is 680K and resistor R67 is 150K. The output of voice amplifier 188 is ac coupled to an audio power amplifier 192 comprising a LM 386N-4 amplifier 194. The power amplifier 194 drives a speaker 196 with the filtered and amplified voice signal output of the processor 170 (FIG. 10).

As each power setting is transmitted by the microprocessor 28 over the data bus, the setting appears at the BUS 0–7 inputs of the speech synthesizer processor 170, and the speaker 196 sounds the power setting as it is displayed on LED display 16. For example, the LED display and synthesizer display and sound the power settings "2", "4", "6", "8", "10", "15", "20", "25", "30", "35", "40", "45", "50", "60", "70", "80", "90", "100", "110", "120", "130", "140", "150". Each setting is non-dimensional but corresponds to a particular AGC DAC 140 input and output, as described previously, hence a particular RF power output level.

N4/AGC LOOP

The N4 output of the N-line decoder 158 (FIG. 8) is connected to the DAC 140 in the AGC 44 (FIG. 7). The N4 output controls the write enable ($\overline{WR}$) input of the DAC. When the N4 output is high, the $\overline{WR}$ input of the DAC is low, due to the inverter 196. The DAC writes the hexadecimal power setting on the microprocessor data bus into its BUS 0–7 inputs. The VREF output of the DAC is the analog input to the amplifier 152. The level of the VREF output is equal to K/256×200 millivolts, where K is the decimal equivalent of the power setting.

N5,N6/CUT/COAG CONTROL FLIP-FLOP

The N5 and N6 outputs of the decoder 158 operate the cut/coag control flip-flop 40. See FIG. 8A. Flip-flop 40 is a CD4013BE dual D type flip-flop. The N5 output controls the preset (P) input of the flip-flop. When the N5 output is high, it presets the flip-flop so that the Q output is high and the $\overline{Q}$ output is low. The Q and $\overline{Q}$ outputs of the flip-flop should not be confused with the Q output generated by the microprocessor 28. The microprocessor Q signal turns the waveform generator on or off, whereas the Q, $\overline{Q}$ outputs of flip-flop 40 indicate whether operation is in the Coagulate or Cut mode.

The N6 output controls the reset (R) input of flip-flop 40. When the N6 output is high, it resets the flip-flop so that the Q output is low and the $\overline{Q}$ output is high. The N5, N6 signals are complementary signals, as are the Q and $\overline{Q}$ outputs of the flip-flop.

The Q output of the flip-flop drives a NAND gate 196 which operates as a buffer driver for transistor Q6 and the "cut" LED 18. See FIG. 8B. When the Q output of the flip-flop is low, indicating operation in the Cut mode, NAND gate 196 turns transistor Q6 on so as to illuminate "cut" LED 18 on the front panel. When the $\overline{Q}$ output of the flip-flop is low, indicating operation in the Coagulate mode, NAND gate 198 turns transistor Q7 on so as to illuminate "coag" LED 20 on the front panel.

The Q, $\overline{Q}$ outputs of flip-flop 40 also control the burst randomizer 52, the cut/coag gating circuit 140, the power cycling circuit 62 and the tone generator 36.

BURST RANDOMIZER

Figure 5:
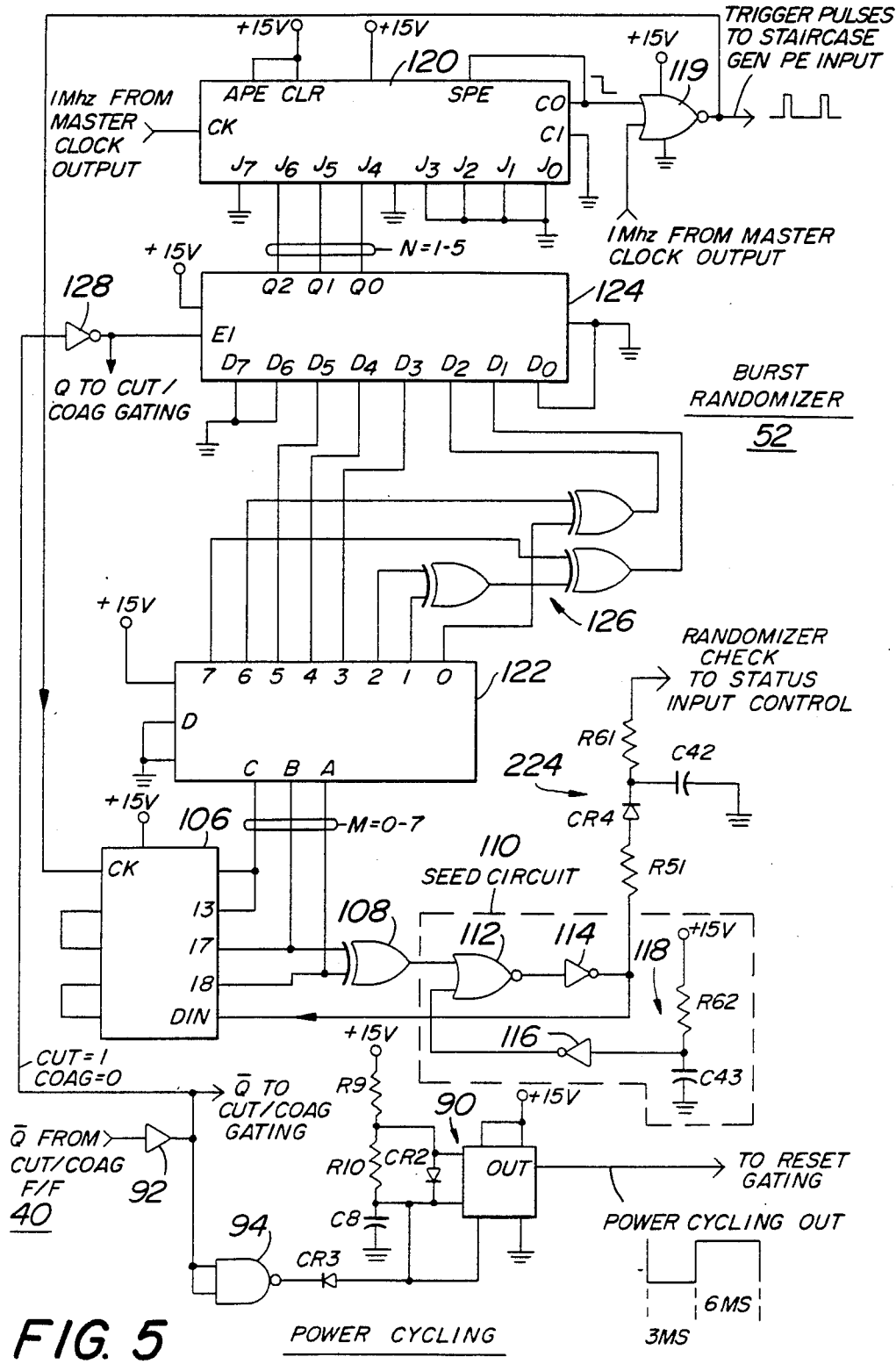
FIG. 5 is a circuit schematic of the remainder of the waveform generator section.

The $\overline{Q}$ output is transmitted by driver 92 to inverter 128 in the burst randomizer circuit 52 (FIG. 5). The inverter output inhibits the priority encoder 124 when the $\overline{Q}$ output is high, indicating operation in the Cut mode. When the encoder is inhibited, the Q0–Q2 outputs 124 cause the divide by 10N+1 circuit 120 to pass the 1 Mhz master clock pulses directly to NOR gate 119. The output of the NOR gate is therefore a stream of 1 Mhz pulses, as previously described, which serve as the trigger pulses for the waveform generator section 34 (FIG. 4). The output of the waveform generator section is therefore a steady stream of uniform amplitude 1 Mhz analog pulses.

In the Coagulate mode, the $\overline{Q}$ output is low, and the priority encoder operates as already explained to generate the aperiodic trigger pulses at the burst randomizer output. The output of the waveform generator is therefore an aperiodic sequence of ramped analog pulse bursts.

POWER CYCLING

During the Cut mode, $\overline{Q}$ output also inhibits the timer 90 in the power cycling circuit 62 (FIG. 5) via NAND gate 94. The output of the timer 90 is held high so that there is no power cycling waveform in the Cut mode. Accordingly the 1 Mhz analog pulses generated by the wave form generator section 34 are not interrupted by a power cycling dead zone.

In the cut mode, moreover, the Q output is low, disabling NAND gate 88 in cut/coag gating circuit 140. See FIG. 4. The frequency swept 1 Mhz signal, then, is not transmitted to the D/A gating circuit 56. Instead, the $\overline{Q}$ output, which is high, enables NAND gate 104 to pass the 1 Mhz master clock pulses to the D/A gating circuit 56 via NAND gate 78. In the cut mode, then, driver 58 transmits a steady stream of uniform amplitude pulses, there being no bursts, no power cycling off time or dead zone, and no frequency sweeping.

In the Coagulate mode, the $\overline{Q}$ output is low, enabling the timer 90 (FIG. 5) to free-run, and the power cycling circuit produces the power cycling waveform. In addition, the Q output is high, thereby enabling NAND gate 88 in cut/coag gating 140 to pass the frequency swept 1 Mhz signal to D/A gating circuit 56 via NAND gate 78. See FIG. 4. In the same mode, the $\overline{Q}$ output is low, disabling NAND gate 104. In the Coagulate mode, then, driver 58 produces the aperiodic, pseudo-random sequences of bursts of ramped pulses according to the power cycling waveform, and the frequency of the ramped pulses is swept between 4% below and above the 1 Mhz frequency.

TONE GENERATOR AND AUDIO CONTROL CIRCUIT

Figure 11:
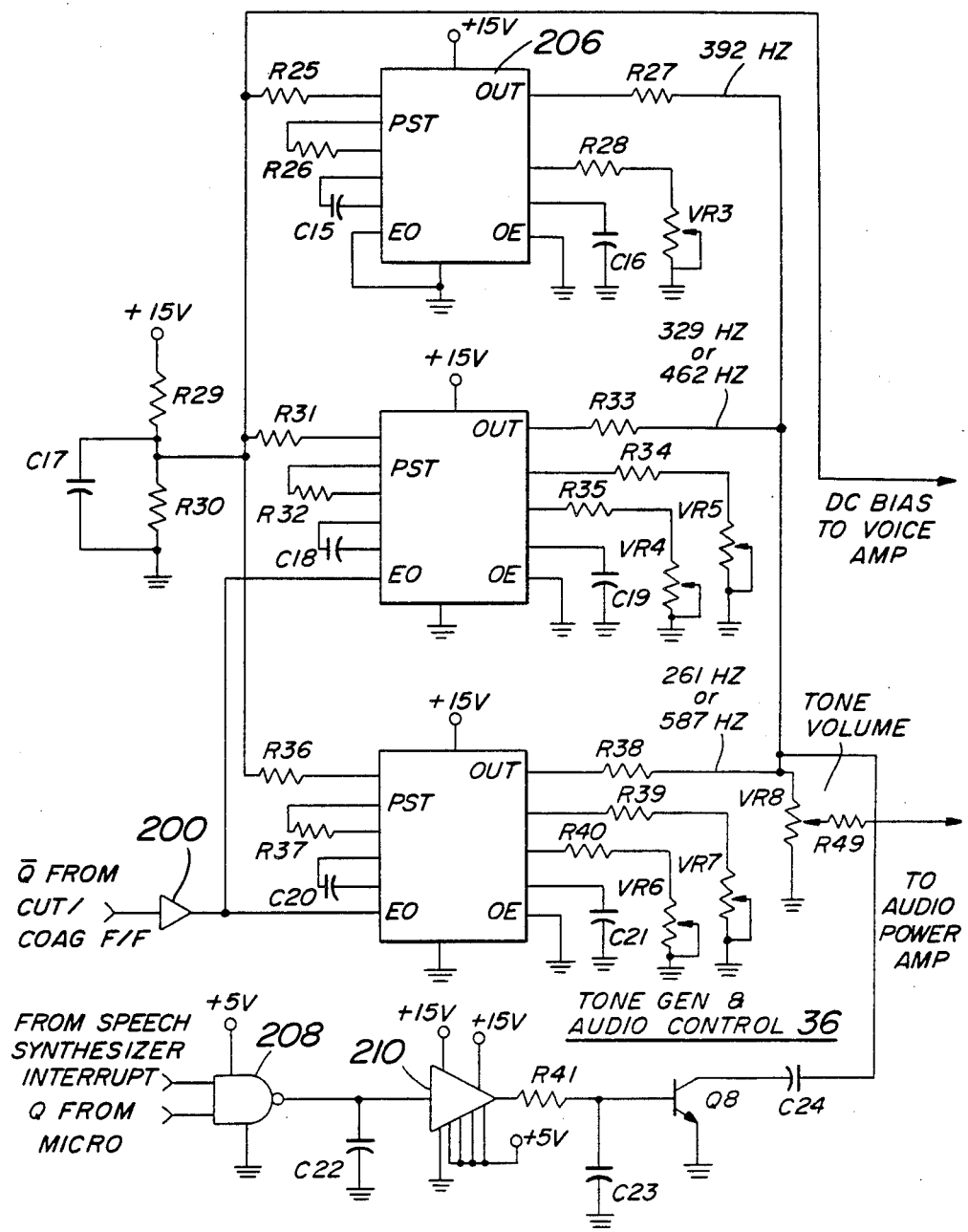
FIG. 11 is a circuit schematic of the tone generation and audio control.

The tone generator and audio control circuit 36 is shown in detail in FIG. 11. The $\overline{Q}$ output of the cut/coag flip-flop is transmitted by a CD 40109 driver 200 to the enable (E0) input of XR2206CP function generators 202, 204. In the Coagulate mode, the $\overline{Q}$ output is low, causing function generator 202 to generate a 261 Hz sine wave at its output (OUT). In addition, the low $\overline{Q}$ output causes the function generator 204 to generate a 329 Hz sine wave at its output (OUT). The 261 Hz and 329 Hz sign waves are mixed at a 50K tone volume potentiometer VR8. A 392 Hz sine wave signal is continuously generated by a third XR2206CP function generator 206 and is mixed with the 261 Hz and 329 Hz signals at the tone volume potentiometer VR8. The three mixed signals are transmitted at the potentiometer setting to the inverting input of operational amplifier 194 in the audio power amplifier circuit 192 (FIG. 12). The speaker 196 sounds a major chord corresponding to the mixed sine signals thereby indicating to the surgeon that operation is in the Coagulate mode.

When the $\overline{Q}$ output is high, indicating operation in the Cut mode, the function generator 202 generates a 587 Hz sine wave at its output and function generator 204 generates a 462 Hz sine wave at its output. The 587 Hz and 462 Hz signals are mixed together with the 392 Hz output of function generator 206 to produce a tone volume potentiometer VR8 output corresponding to a minor chord. The composite signal is amplified by power amplifier 194 and sounded as a minor chord by speaker 196 indicating to the surgeon that operation is in the cut mode.

Thus, the major chord is continuously sounded in the Coagulate mode and that the minor chord is continuously sounded in the Cut mode as indicated below:

| Q | Mode | Chord |
|---|------|-------|
| 0 | coag | major = 261 hz + 329 hz + 392 hz |
| 1 | cut  | minor = 587 hz + 462 hz + 392 hz |

Provision is made for interrupting the major or minor chords under four conditions. First, if a malfunction of the burst randomizer 52 is detected by the microprocessor 28, as described hereinafter, the microprocessor Q output is switched low. The condition is detected by NAND gate 108 in the tone generator and audio control circuit 36 (FIG. 11). The NAND gate generates a high signal at the input of a CD 40109 driver 210 which turns transistor Q8 on, clamping the tone volume potentiometer VR8 to ground. This prevents a major or minor chord from being sounded until the malfunction is eliminated.

Second, when a voice message is being sounded, the Interrupt output of the speech synthesizer processor 170 is driven low, causing NAND gate 208 and driver 210 to turn on transistor Q8 thereby clamping the tone volume potentiometer VR8 to ground, preventing sounding of a major or minor chord. The speech synthesizer Interrupt output goes low while analog voice data is being transmitted at the output of processor 170 to the voice filter and amplifier circuit 38. When transmission of the voice data is completed, the speech synthesizer Interrupt returns to a high level, and NAND gate 208 and driver 210 turn off transistor Q8, freeing the tone volume potentiometer VR8. The tone volume potentiometer VR8 resumes transmission of the major or minor chord signals to the audio power amplifier 192, and the major or minor chord is sounded by the speaker 196.

Third, when power is lost at the RF power output due to a blown fuse in the power supply, as described hereinafter, the condition is indicated by a microprocessor Interrupt circuit 234 (FIG. 8), and the microprocessor switches its Q output low. As a result, the tone volume potentiometer VR8 (FIG. 11) is clamped to ground, preventing a major or minor chord from being sounded until the fuse is replaced.

Fourth, when the footpedal connection is removed (as described hereinafter), the condition is indicated by the microprocessor. As a result, the tone volume potentiometer VR8 (FIG. 11) is clamped to ground, preventing a major or minor chord from being sounded until the footpedal is re-connected.

Thus, a voice message from the speech synthesizer to indicate a power setting, a malfunction of the burst randomizer, loss of power output, or disconnection of the footpedal, result in temporary interruption of the major or minor chord. Once the voice message is completed or the malfunction or other condition is corrected, the major or minor chord is restored at the speaker.

N7/STATUS INPUT CONTROL

The N7 output of the N-line decoder controls status input control circuit 212. See FIG. 12. The status input control provides status inputs to the microprocessor 28 indicative of the state of the power up/down switch 14, malfunction of the burst randomizer circuit 52, and disconnection of the cut/coag foot pedal.

Specifically, the status input control circuit 212 is controlled by the microprocessor memory write ($\overline{MWR}$) output and the N7 output of the N-line decoder 158 (FIG. 8). The $\overline{MWR}$ output of the microprocessor is generated at appropriate times during each cycle of the program to enable the microprocessor to receive input data. The $\overline{MWR}$ and N7 signals are processed by NAND gates 214, 216 and 218 to enable the CD4016BE quad transmission gates 146, 220 and 222 to transmit the up/down Direction, Randomizer Check and Footpedal Check signals to the microprocessor BUS 0, 1 and 2 data inputs. When the N7 signal is high and the MWR signal is low, NAND gates 214, 216 and 218 set the enable (EN) inputs of transmission gates 146, 220 and 222 at a high level, enabling the transmission gates. The data at the outputs of the transmission gates is stored in an accumulator register in the microprocessor. When the gates are disabled, by a low NAND gate 218 output, the inputs and outputs of the gates are effectively disconnected and ignored by the microprocessor.

POWER UP/DOWN SWITCH INTERFACE

The input to status input control gate 146 is the Direction signal output from the power up/down switch interface (FIG. 13). When the power up/down switch is in the "up" position, opto-isolator Q9 is off so that the Direction signal is pulled high, and opto-isolator Q10 is on so that the Strobe output signal is low. The Direction signal is transmitted by status input control gate 146, as previously described, to the BUS 0 data input of the microprocessor 28 (FIG. 8). The Strobe signal is transmitted directly to the external flag input EF4 of the microprocessor. In response to the BUS 0 and EF4 inputs, the microprocessor sequentially addresses the EPROM 142 via the microprocessor memory address lines MA 0-7 and the address decoder 144 output lines Q1-Q3.

In particular, the microprocessor addresses a power setting table in the EPROM, and the EPROM transmits a sequence of digital words of consecutively increasing value over the microprocessor data bus to the AGC DAC 140 (FIG. 7) so long as the power switch 14 remains in the up position. Each word represents a discrete power setting. The words are also transmitted to the display 16 (FIG. 9) and to the speech synthesizer 30 (FIG. 10). Transmission of the power setting words to the DAC 140, display 16, and speech synthesizer 30 takes place simultaneously over the microprocessor data bus. Each setting is displayed by the display digits A-C and is sounded by the speaker. When the desired power setting is reached, the operator releases the power up/down switch 14 so that the switch returns to the neutral position.

In the neutral position, opto-isolators Q9 and Q10 are turned off. The Direction signal therefore remains high, while the Strobe signal changes from low to high. The change in the Strobe signal is detected by the microprocessor at the EF4 input, terminating the EPROM 142 adressing sequence. The EPROM BUS 0-7 outputs remain at the last or selected power setting.

When the power up/down switch 14 is in the "down" position, opto-isolaters Q9 and Q10 (FIG. 13) are on. The Direction signal is low, as is the Strobe signal. The microprocessor 28 reverses the sequence of addressing EPROM 142 so that the EPROM transmits a sequence of digital words representing consecutively decreasing power settings at the EPROM BUS 0-7 outputs. The power settings are transmitted over the microprocessor data bus, and they are displayed, sounded and transmitted to the AGC DAC 140 as previously described. When the desired power setting is reached, the operator releases the power up/down switch, the switch returns to the neutral position, both optoisolaters Q9, Q10 go off, and the Direction and Strobe signals change from low to high. The change in the Strobe signal is detected at the EF4 input of the microprocessor, the microprocessor terminates the EPROM addressing sequence, and the EPROM maintains its BUS 0-7 outputs at the last or selected power setting.

RANDOMIZER CHECK

When status input control gate 220 (FIG. 12) is enabled, the gate transmits the Randomizer Check signal to the BUS 1 input of microprocessor 28. The Randomizer Check signal is generated by a diode-RC circuit 224 in the burst randomizer circuit 52. See FIG. 5. The diode RC circuit 224 comprises resistors R51, R61, capacitor C42 and diode CR4 having the following values:

| R51 | R61 | C42 |
| --- | --- | --- |
| 27K | 100K | .01 uf |

The input to the diode-RC circuit is the seed circuit 110 output.

Once capacitor C43 of the RC charging circuit 118 (FIG. 5) is charged so as to switch the inverter 116 output from high to low, the output of the seed circuit 110 merely follows the output of exclusive OR gate 108. The output of the seed circuit therefore remains high so long as one and only one of the exclusive OR gate inputs is high. If both inputs are high or if both inputs are low, the output of the seed circuit will change from high to low. If both exclusive OR gate inputs remain high or both remain low for an unacceptably long period of time, this indicates that the outputs of shift register 106 have effectively lost their random character. The diode-RC circuit 224 sets the minimum acceptable period of time during which both exclusive OR gate inputs are permitted to remain high or low. The duration is effectively set by the resistor R61 and capacitor C42. In the preferred embodiment described herein, time period required for the capacitor to discharge to the low output of seed circuit 110 is approximately 100K×0.01 microfarads=1 millisecond. This is 1/6th of the time of the power cycling waveform.

Accordingly, if both exclusive OR gate inputs remain either high or low for 1/6th or more of the on time of the power cycling waveform, the diode-RC circuit 224 produces a low Randomizer Check signal.

The microprocessor detects the low level at the BUS 1 input and enters an error routine. As described hereinafter, in this routine the microprocessor switches its Q output signal low and generates a digital word on the BUS 0-7 outputs which is an error message for the display 16. The error message may, for example, cause the display to display the number "200" to indicate the error condition at the burst randomizer circuit. Preferably, the error message is repetitively generated so that the number, such as "200", is flashed on the display 16. As part of the error routine, the microprocessor 28 also generates an error message which is transmitted over the microprocessor data bus to the BUS 0-7 inputs of the speech synthesizer processor 170 (FIG. 10). In response to the error message, the processor 170 addresses EPROM 172 so as to retrieve digitized speech which represents a voice signal message "Recycle Power". The digitized data is processed by the processor 170, and the processor generates a voice signal at its output which is used by the voice filter and amplifier circuit 38 to sound the voice message. The error message transmitted to the speech synthesizer processor 170 may be repeated so as to repetitively announce the voice message until the malfunction is corrected.

In addition, when the microprocessor Q output signal is switched low in response to a low Randomizer Check signal, transistor Q5 (FIG. 7) is switched on, clamping the inverting input of amplifier 152 to +15 volts. The output of the amplifier 152, which is the voltage control output of the AGC circuit, is therefore clamped to ground. The buffers 68 (FIG. 4) therefore do not transmit the counter 72 outputs to the resistive ladder network 66, thereby disabling driver transistor Q3 so that the driver 58 output is clamped to ground and the RF power output section is disabled.

From the foregoing, it should be appreciated that upon detection of an error condition in the burst randomizer circuit, error messages are displayed on display 16 and sounded by speaker 196 while the waveform generator and RF power output sections are disabled. Accordingly, the surgeon is immediately notified of the error condition, visually and by sound, and the power output is removed so that no damage can be done to vessels or tissue due to the lack of aperiodicity of the power output.

To resume operation, the surgeon must move the power on/off switch 12 to the "off" position and then restore the switch to the "on" position. When the switch is returned to the "on" position, the seed circuit 110 (FIG. 5) reseeds the shift register 106, in the manner previously described, enabling the burst randomizer and associated circuitry to function in the normal manner so that aperiodic bursts of RF again appear at the RF power output.

FOOTPEDAL CHECK

Figure 14:
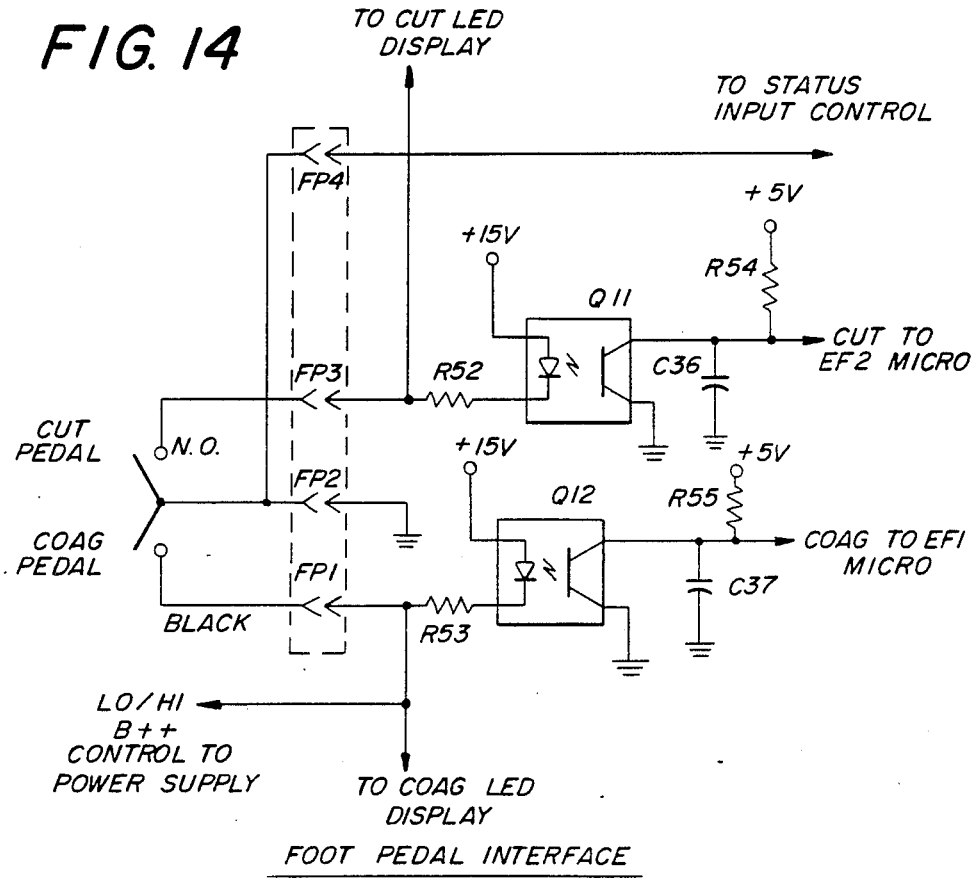
FIG. 14 is a circuit schematic of the foot pedal interface.

The status input control 212 monitors the footpedal interface (FIG. 14) to determine whether the footpedal 226 has been properly connected to the interface. If the footpedal is properly connected to the interface, jack contacts FP 1-4 are closed. Contacts FP 2 and FP 4 are therefore tied to ground, clamping the Footpedal Check output line to ground. The cut pedal and coag pedal contact arms are electrically connected to the FP 2 contacts and are also clamped to ground. The status input control gate 222 transmits the low or ground level at the Footpedal Check line to BUS 2 input of the microprocessor. The low level indicates that the foot pedal is properly connected to the interface, and the microprocessor operates in the manner already described to produce the appropriate power output signals in the cut or coagulate modes.

If the foot pedal is not properly connected to the interface, the FP 2 contacts will be open. The Footpedal Check output line is therefore floating, and the pull up resistor R69 at the input of status input control gate 222 (FIG. 12) produces a high level at the gate input. The gate transmits the high level to the BUS 2 input of the microprocessor. In response, the microprocessor enters an error routine, generating data on the microprocessor data bus which causes the display 16 to flash the error message "300" and which causes the speech synthesizer circuit 30, voice filter and amplifier circuit 38 and speaker 196 to repeatedly sound the error message "Foot Pedal". The visual and audible error messages are repeated until the foot pedal is properly connected to the foot pedal interface.

CUT AND COAG MODE SIGNALS

The foot pedal interface includes 4N 37 opto-isolaters Q11, Q12. The opto-isolaters transmit the Coag and Cut mode signals respectively to the external flag inputs EF1, EF2 of the microprocessor.

To operate in the Cut mode, the cut pedal contact arm is depressed so as to ground resistor R52 (FIG. 14) through the circuit path comprising contacts FP3, the cut pedal contact arm and contacts FP2. The Cut mode signal output of the opto-isolater is therefore clamped to ground. The microprocessor detects the low level of the cut mode signal at the EF2 input and enters a CUT routine described hereinafter. In the CUT routine, the continuous RF cut waveform is generated at the power output section as previously described.

To operate in the Coagulate mode, the coag pedal contact arm is depressed so as to create a circuit path comprising contacts FP1, the coag pedal contact arm and contacts FP2. This grounds resistor R53 at the opto-isolater Q12 input. The Coag mode signal output of the opto-isolater is therefor clamped to ground. The microprocessor detects the low level of the Coag mode signal at the EF1 input and enters a COAG routine described hereinaftaer. In the COAG routine, the RF power output section produces the aperiodic bursts of frequency swept RF signals as previously described.

POWER SUPPLY

The power supply includes a conventional +5 volt regulated dc supply and a conventional +15 volt regulated dc supply (not shown). The +5 volt and +15 volt supply voltages are provided to the circuit components in conventional manner.

Figure 15:
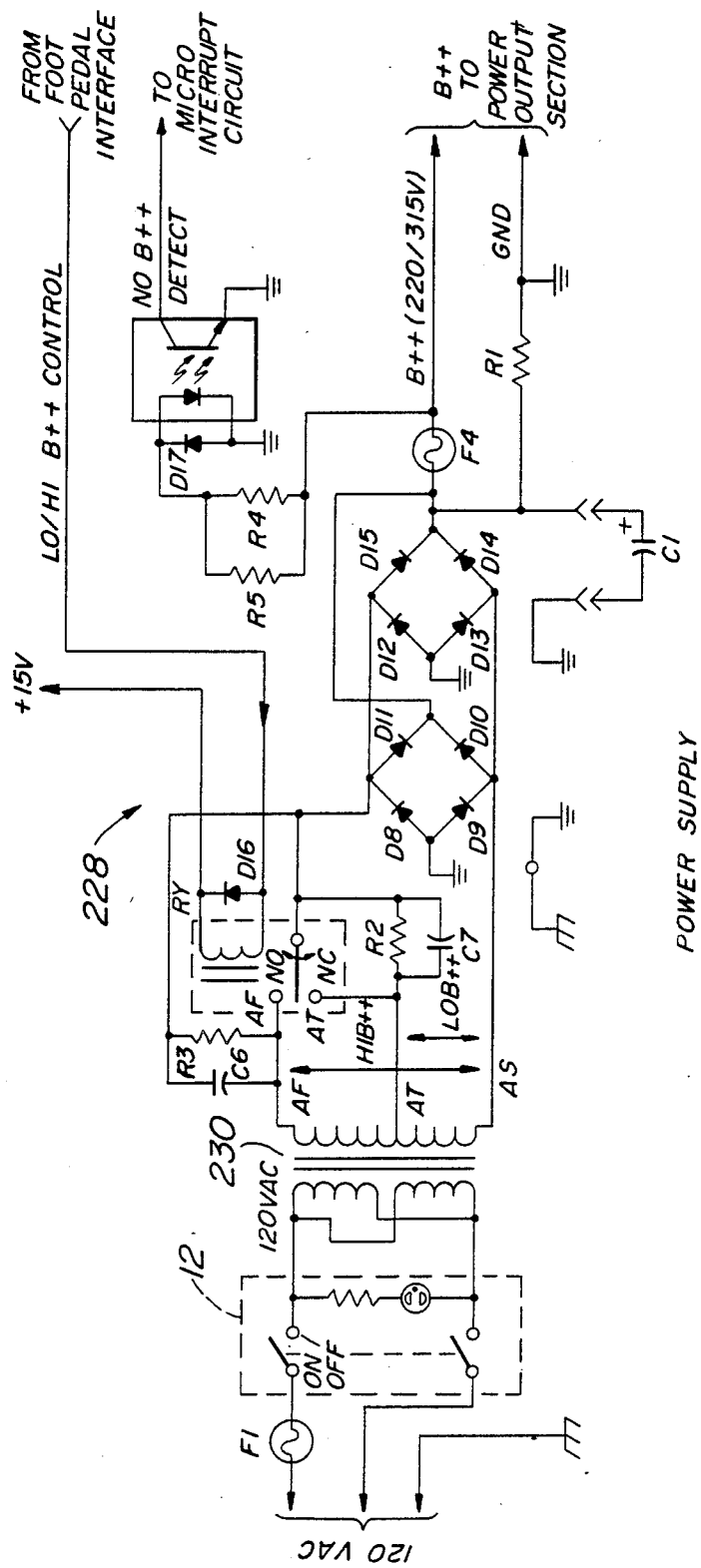
FIG. 15 is a circuit schematic of a portion of the power supply.

The power supply also includes low/high switching circuitry and error detection circuitry generally designated 228 in FIG. 15. Circuit 228 includes a relay Ry having a contact arm which is normally closed at the low voltage contact AT of the line transformer 230 secondary. If neither the cut nor coag pedal contact arms are depressed, or if only the cut pedal contact arm is depressed, the LO/HI B++ signal (FIG. 14) is high, and the relay Ry arm (FIG. 15) stays at the AT contact. Circuit 228 therefore develops a 220 volt (LO B++) signal at the B++ output line. The B++ output line is connected to the tank circuit 64 in the RF power output section (FIG. 3) so that the LO B++ signal powers the power MOSFETs Q1, Q2. The amplitude of the continuous RF signal developed at the secondary of the RF power output section transformer T1 in the Cut mode is therefore directly proportional to the amplitude of the LO B++ signal.

If the coag pedal contact arm is depressed, or if both the coag and cut pedal contact arms are depressed, the LO/HI B++ control signal (FIG. 14) is clamped to ground. The LO/HI B++ control signal operates the relay Ry so that the relay contact arm transfers to the high voltage AF contact of the line transformer 230 secondary. See FIG. 15. For this condition, the circuit 228 develops a 315 volt (HI B++) signal on the B++ line output. The HI B++ signal now powers the MOSFETs Q1, Q2 (FIG. 3). The envelopes of the aperiodic RF bursts developed at the secondary of the RF power output section transformer T1 in the Coagulate mode are therefore directly proportional to the HI B++ signal.

From the foregoing, it should be appreciated that, for equal power settings, the ratio of the amplitudes of the RF signal developed in the Cut mode to the initial or peak value of an RF burst developed in the Coagulate mode is given by the ratio LO B++/HI B++ or 220/315. Thus, the amplitude of the RF output developed by the power output section is automatically switched to ensure the most efficient waveform for operation in the Coagulate and Cut modes, minimizing the danger of damage to vessels or tissue in either mode.

If both the coag and cut pedal contact arms are depressed simultaneously, the coag pedal contact arm governs and the device operates in the Coagulate mode. Thus, for this condition, both the EF1 and EF2 inputs to the microprocessor 28 (FIG. 8) are low, and the microprocessor is programmed to enter the COAG routine corresponding to operation in the Coagulate mode. Moreover, for this condition, the LO/HI B++ control signal (FIG. 14) is clamped to ground by the coag pedal contact arm, and the relay Ry (FIG. 15) is operated to provide a HI B++ (315 volts) signal at the B++ line output. Since the HI B++ signal appears at the MOSFETs drains (FIG. 3) the RF signal output at the transformer T1 secondary is directly proportional to the HI B++ signal.

NO B++ DETECT

The power supply circuit 228 includes a 1.5 amp fuse F4 coupled to No B++ Detect circuitry comprising an opto-isolater Q13. The output of the opto-isolater is the No B++ Detect line which is connected to NAND gate 232 in the microprocessor Interrupt circuit 234 (FIG. 8). Overcurrent on the B++ output line of power supply 228, which blows or opens the fuse F4, turns the opto-isolator off. The No B++ Detect output line of the opto-isolater Q13 therefore floats, and NAND gate 230 generates a low level at the microprocessor Interrupt input. The microprocessor senses this condition and enters an INTERRUPT routine as described hereinafter. In the INTERRUPT routine, the microprocessor generates data on the data bus so as to cause the display 16 to flash the error message "00" while causing the speech synthesizer circuit 30 to repeatedly sound the error message "Internal Fuse". In addition, the microprocessor switches its Q output low thereby turning off the LED 102 (FIG. 4), the staircase generator circuit 54 (FIG. 4), and the tone volume potentiometer VR8 (FIG. 11). Accordingly, the RF output waveform produced by the RF power output section and the chord generated by the tone generator and audio control 36 are interrupted. Operation can resume, with power output and chord generation, when fuse F4 is replaced and the power on/off switch is thrown off and then on.

When fuse F4 is replaced, the optoisolater Q13 is again turned on, clamping the No B++ Detector line to ground (FIG. 15). The microprocessor Interrupt circuit 234 therefore generates a high level at the microprocessor Interrupt input, and the microprocessor exits the INTERRUPT routine.

OPERATION/SOFTWARE

The programming or software for the microprocessor 28 is shown in detail in the flow charts in FIGS. 16A–C and 17A–B. Initially, the microprocessor enters the START routine wherein the microprocessor Interrupt input is disabled and the program counters and index registers are initialized. The microprocessor then commands the N-line decoder 158 to generate a high N5 output which presets the cut/coag control flip-flop 40 (FIG. 8). The Q output of the flip-flop is therefore high, indicating operation in the Coagulate mode. After a 320 milisecond delay, the microprocessor calls the RANDOMIZER CHECK routine wherein the MWR and N7 signals are generated to enable the status input control 212 to transmit the RANDOMIZER CHECK signal to the BUS 1 input of the microprocessor.

Figure 17A:
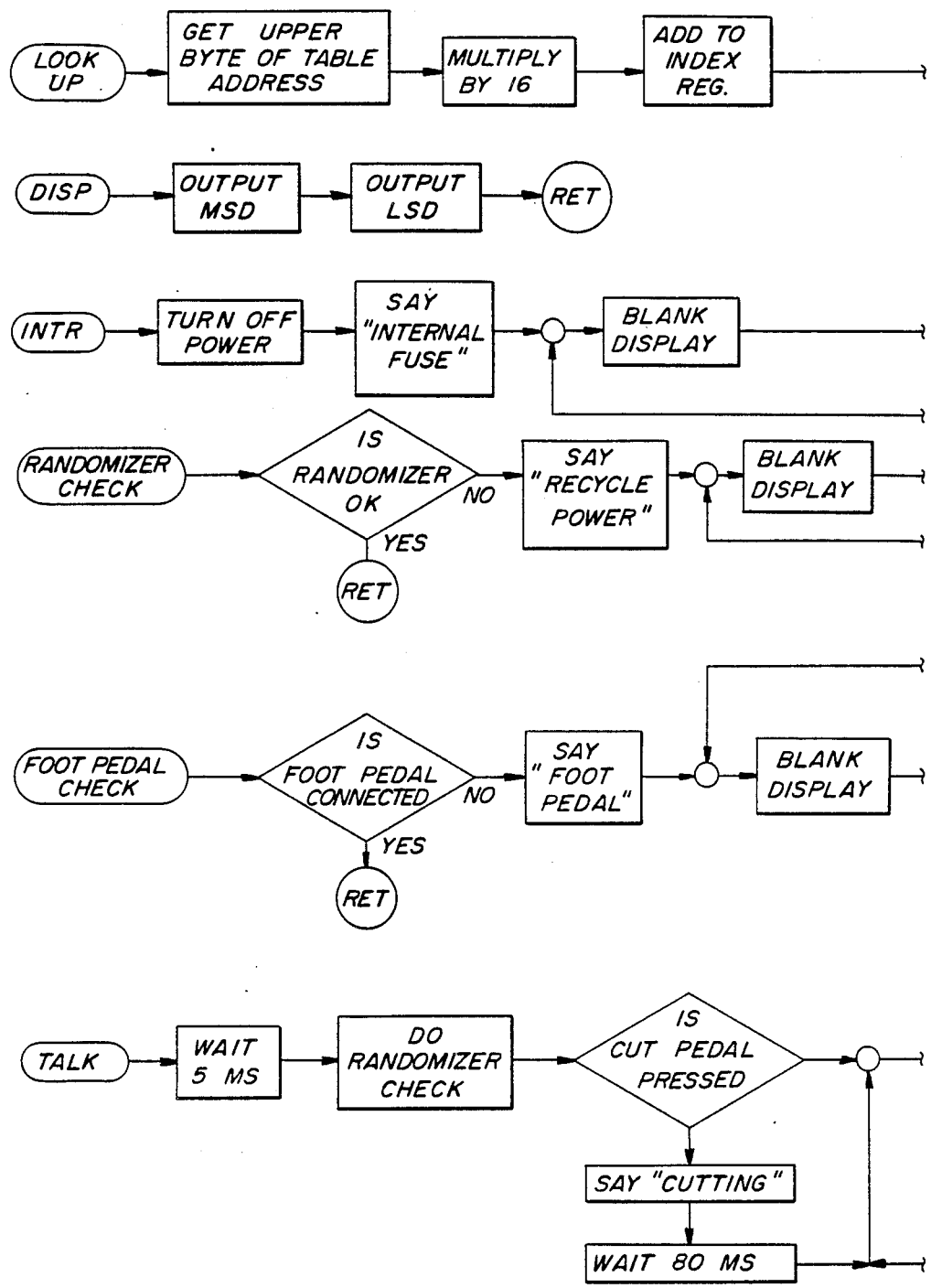

The RAMDOMIZER CHECK routine is shown in FIGS. 17A and B. If the RANDOMIZER CHECK signal indicates an error condition, the microprocessor causes the speech synthesizer 30 to repeatedly sound the error message "Recycle Power" as previously described. In addition, the microprocessor enters a "FLASH 200" loop wherein it causes the display 16 to flash the error message "200" by blanking the display for 160 miliseconds and displaying the error message for 320 milliseconds repeatedly until the RANDOMIZER CHECK signal indicates no error condition. If no error condition is indicated by the RANDOMIZER CHECK signal, the microprocessor leaves the RANDOMIZER CHECK routine and returns to the START routine.

Figure 16A:
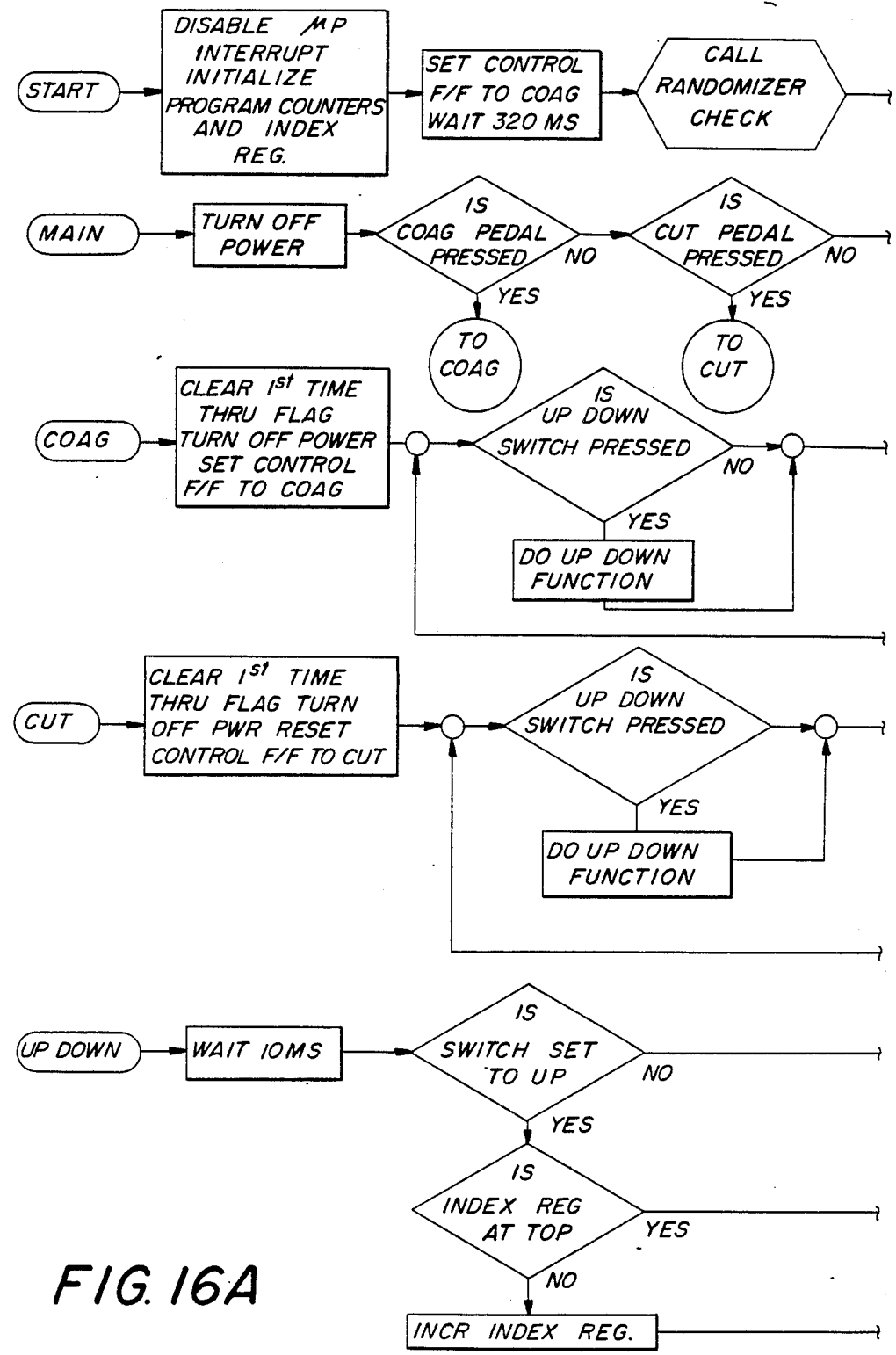
FIGS. 16A-16C and 17A and 17B comprise a flow chart of the software.
Figure 16B:
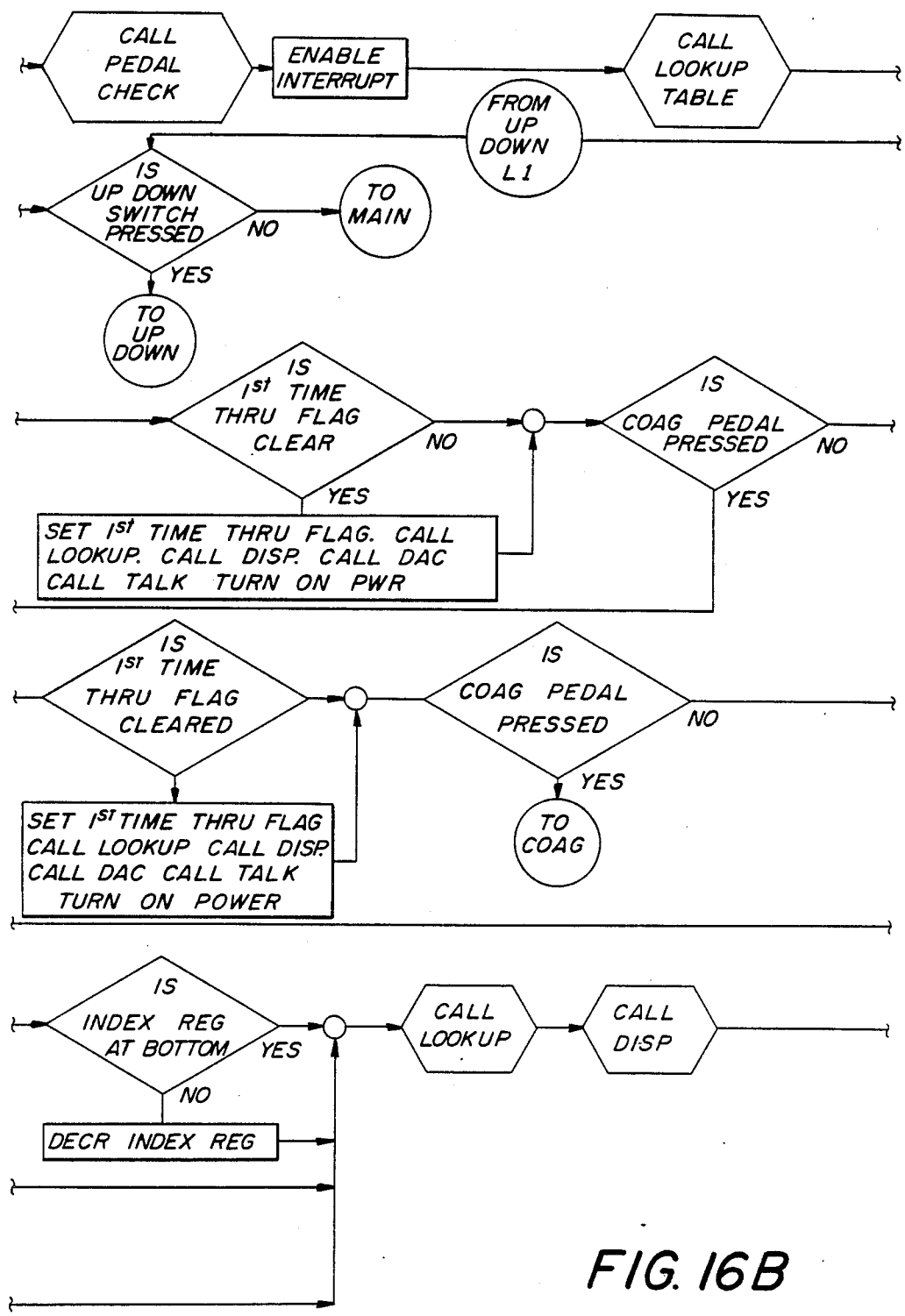
Figure 17B:
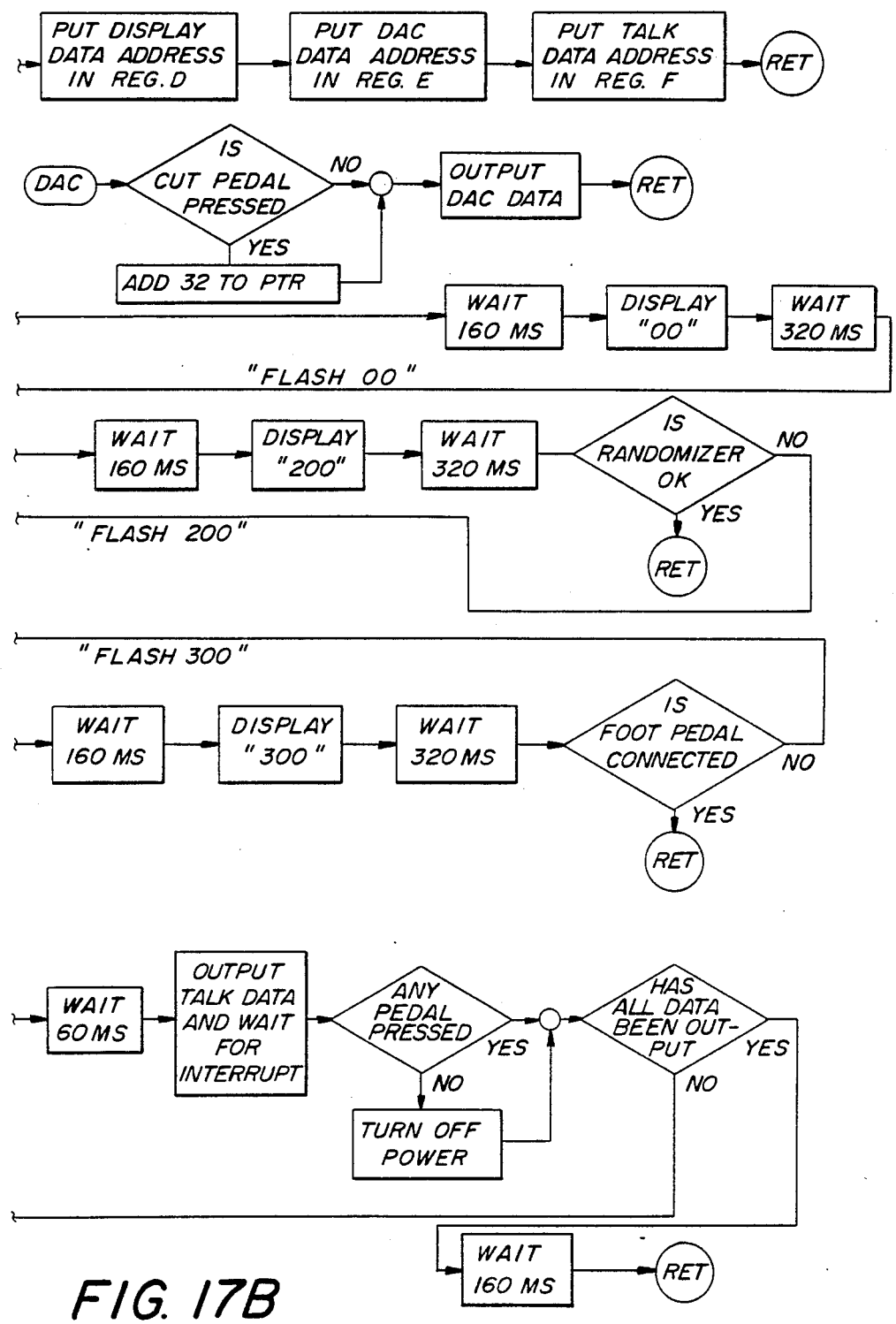

The microprocessor then enters the CALL FOOTPEDAL CHECK routine (FIG. 16B). The CALL FOOTPEDAL CHECK routine is shown in FIGS. 17A–B. In this routine, the microprocessor generates the MWR and N7 signals so that the status input control circuit 212 can transmit the Footpedal Check signal to the BUS 2 input of the microprocessor. If the Footpedal check signal indicates an error condition, namely that the foot pedal 226 is disconnected, the microprocessor causes the speech synthesizer, voice filter and amplifier and speaker to repeatedly sound the error message "Foot Pedal". In addition, the microprocessor enters a "FLASH 300" loop wherein the display is repeatedly blanked for 160 milliseconds and caused to display the error message "300" for 320 milliseconds. If the Footpedal Check signal indicates the footpedal is connected properly, the microprocessor exits the FOOTPEDAL CHECK routine and returns to the START routine.

The microprocessor then enables its Interrupt input (FIG. 16B) and calls the lookup table addresses for EPROM 142 (FIG. 8). The lookup table contains the data for the display 16, AGC DAC 140 (FIG. 7) and speech synthesizer processor 170 (FIG. 10) as previously indicated. The LOOKUP TABLE routine is shown in FIG. 17–B. In this routine, the microprocessor generates the a for the relevant portions of the EPROM lookup table by fetching the upper byte of the microprocessor index register, multiplying the address by 16, and adding the product to the index register. The microprocessor stores the EPROM for the display portion of the lookup table in a "D" register, stores the EPROM address for the AGC DAC portion of the lookup table in a "E" register, and stores the EPROM address for the speech synthesizer processor portion of the lookup table in the "F" register. The "D", "E" and "F" registers are internal registers in the microprocessor 28. Thus, in the LOOKUP routine, the microprocessor stores EPROM addresses for the display, DAC, and speech synthesizer portions of the EPROM lookup table. The microprocessor then returns to the START routine.

Figure 16C:
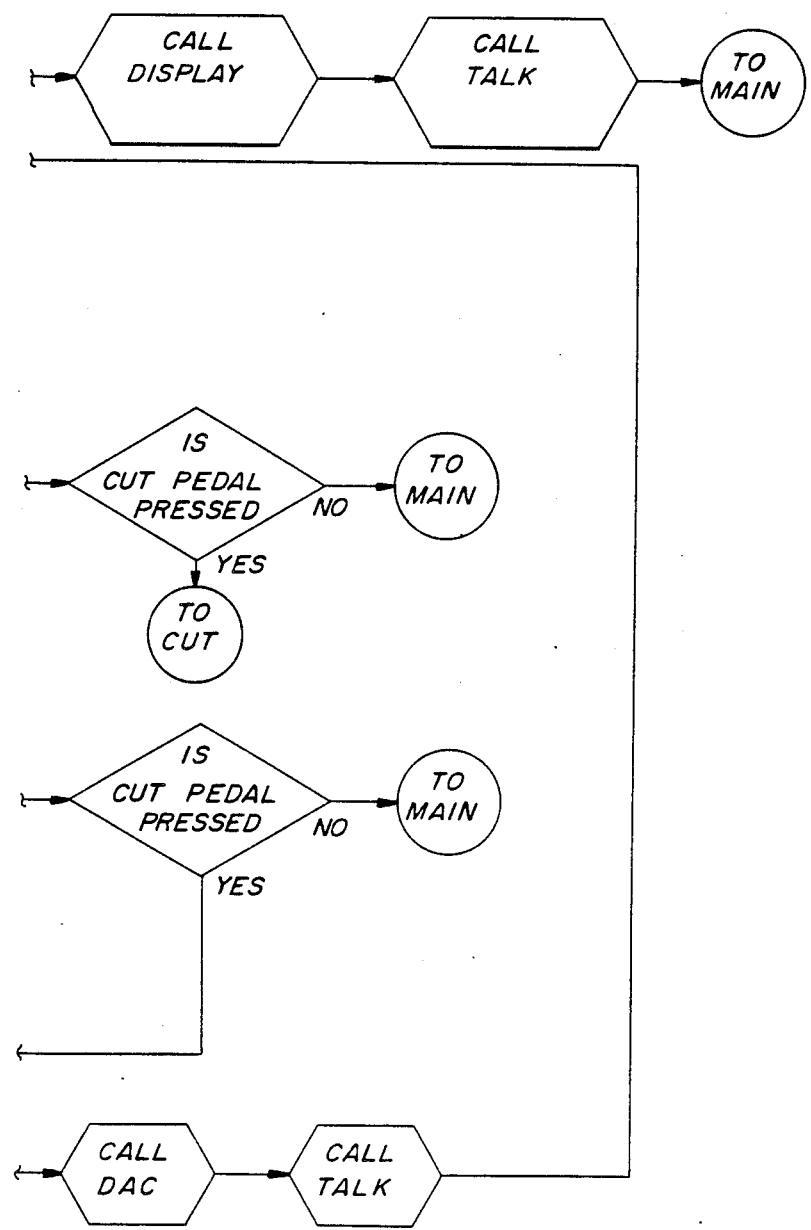

The microprocessor then calls the DISPLAY routine. (FIG. 16C). In this routine, the microprocessor commands the N-line decoder 158 to generate the N1 and N2 signals. The $\overline{N1}$, $\overline{N2}$ signals are inverted by inverters 160, 162 (FIG. 8) to generate the complements N1, N2 which control the latch decoder drivers 164, 166, 168 in display 16 (FIG. 9) as previously indicated. The microprocessor transmits the most significant digit and least significant digit of the address of the display portion of the look-up table to display 16 over the data bus lines. The microprocessor then returns to the START routine.

The microprocessor then calls the TALK routine. The TALK routine is shown in FIGS. 17A–B. In the TALK routine, the microprocessor waits 5 milliseconds, performs a randomizer check as in the RANDOMIZER CHECK routine and then scans its EF2 input (FIG. 8) to determine whether the cut pedal has been depressed. If the cut signal (FIG. 14) indicates that the cut pedal has been depressed, the microprocessor retrieves a data word from EPROM 142 which corresponds to the EPROM 172 address for the stored digitized error message "Cutting". The microprocessor transmits the message to the speech synthesizer processor 170 as previously indicated. The microprocessor then waits 80 milliseconds and enters the WAIT 60 MS block (FIG. 17B). If the Cut signal (FIG. 14) had indicated that the cut pedal was not depressed, the microprocessor would have directly entered the WAIT 60 MS block without sounding the message "Cutting". In the WAIT 60 MS block, the microprocessor waits 60 milliseconds and then enters the OUTPUT TALK DATA AND WAIT FOR TALKER INTERRUPT routine. In this routine, the microprocessor transmits the EPROM 172 address from the power setting portion of the lookup table to processor 170 and waits for the processor 170 to output the analog voice data corresponding to the power setting. The microprocessor then waits for the end of the Interrupt output from the speech synthesizer processor. The processor 170 generates the Interrupt signal while it is producing the analog voice data to sound the power setting.

The microprocessor then enters the ANY PEDALS PRESSED block wherein it scans its EF1 and EF2 inputs to determine whether the coag pedal or cut pedal is depressed. If the cut and coag signals (FIG. 14) indicate that neither pedal is depressed, the microprocessor enters the TURN OFF POWER block wherein the Q signal of the microprocessor is switched low, resulting in the cut off of RF output power as previously described. Thus, power output is immediately cut off upon release of a depressed foot pedal. The microprocessor then enters the HAS ALL DATA BEEN OUTPUT block. If the cut or coag pedal has been depressed, the microprocessor would have entered the HAS ALL DATA BEEN OUTPUT block directly. In this block, the microprocessor determines whether all digitized speech data has been accessed from the EPROM 142 corresponding to the current power setting. Thus, certain power settings must be sounded by passing through the OUTPUT TALK DATA block twice. For example, the voice message "Thirty five" comprise the separate messages "Thirty" and "Five" which must be sounded in succession. If all data has not yet been accessed, the microprocessor loops back to the WAIT 60 MS routine and repeats the foregoing functions. If all data has been accessed, the microprocessor waits 60 milliseconds and then returns to the START routine which in turn directs the microprocessor to the MAIN routine (FIG. 16A).

In the MAIN routine, the microprocessor first cuts off the RF power output by generating a low Q output signal and then enters the IS COAG PEDAL PRESSED block. The microprocessor scans its EF1 input to make this determination. If the Coag signal indicates that the coag pedal is depressed, the microprocessor enters the COAG routine. If the Coag signal indicates that the coag pedal is not depressed, the microprocessor enters the IS CUT PEDAL PRESSED block. The microprocessor scans its EF2 input to make this determination. If the Cut signal indicates that the cut pedal is depressed, the microprocessor enters the CUT routine. If the Cut signal indicates that the cut pedal is not depressed, the microprocessor enters the IS UP/DOWN SWITCH PRESSED block. The microprocessor scans its EF4 input to make this determination. If the up/down Strobe signal indicates that the up/down switch is depressed, the microprocessor enters the UP/DOWN routine. Operation in the COAG, CUT and UP/DOWN routines is described hereinafter. If the Strobe signal indicates that the UP/DOWN switch is in the neutral position, the microprocessor returns to the beginning of the MAIN routine and continues to cycle through the routine as described above. In the COAG routine (FIGS. 16A–C) the microprocessor clears a FIRST TIME THRU flag, sets the microprocessor Q signal output low to cut off the RF power output, and sets the cut/coag control flip-flop 40 (FIG. 8) so that the Q output of the flip-flop is high, indicating operation in the Coagulate mode. The microprocessor then enters the IS UP/DOWN SWITCH PRESSED block. If the microprocessor determines that the up/down switch is depressed, it executes the function in the UP/DOWN routine (described hereinafter) and then enters the IS FIRST TIME THRU FLAG CLEAR block (FIG. 16B). If the microprocessor had determined that the up/down switch was in the neutral position, it would have entered the IS FIRST TIME THRU FLAG CLEAR block directly. If the FIRST TIME THRU flag is clear, this indicates that the microprocessor has just entered the COAG routine, and the microprocessor has just entered the THRU flag, calls the LOOKUP, DISPLAY, DAC and TALK routines and then turns on the RF power output by setting the microprocessor Q signal to a high level. The LOOKUP, DISPLAY and TALK routines have already been described. The DAC routine is shown in FIG. 17B.

In the DAC routine, the microprocessor first enters the IS CUT PEDAL PRESSED block. The microprocessor makes a determination, by scanning its EF2 input, as to whether the cut pedal is depressed. If the cut pedal is not depressed, the microprocessor directly enters the OUTPUT DAC DATA block wherein the microprocessor accesses the portion of the EPROM lookup table containing the power setting data for the Coagulate mode. The microprocessor transmits the data to the AGC DAC. If the cut pedal is depressed, however, the microprocessor adds 32 to the index register and then enters the OUTPUT DAC DATA block wherein it accesses the portion of the EPROM lookup table containing the power settings for the Cut mode. The microprocessor transmits the data to the AGC DAC. The microprocessor then returns to the COAG routine, calls the TALK routine, sets the microprocessor Q output signal high to turn on the RF power output, and enters the IS COAG PEDAL PRESSED block (FIG. 16B). The microprocessor scans its EF1 input to make this determination. If the microprocessor determines that the coag pedal is depressed, it returns to the IS UP/DOWN SWITCH PRESSED block and repeats the functions described above.

When the microprocessor re-enters the IS FIRST TIME THRU FLAG CLEAR block, the microprocessor determines that the FIRST TIME THRU flag has been set and proceeds to directly to the IS COAG PEDAL PRESSED block. The microprocessor then cycles through the IS UP/DOWN SWITCH PRESSED, IS FIRST TIME THRU FLAG CLEAR and IS COAG PEDAL PRESSED blocks until it determines that the coag pedal has been released as indicated by the Coag signal at the microprocessor EF1 input. If the coag pedal has been released, the microprocessor proceeds to the IS CUT PEDAL PRESSED block to determine whether the operator has now depressed the cut pedal to switch from the coagulate mode to the cut mode. The microprocessor makes this determination by scanning its EF2 input. If the Cut signal indicates that the cut pedal is not depressed, the microprocessor returns to the MAIN routine. If the microprocessor determines that the cut pedal is depressed, the microprocessor enters the CUT routine.

In the CUT routine (FIG. 16A) the microprocessor first clears the FIRST TIME THRU flag, sets the microprocessor Q output low to turn off the RF power output, and resets the cut/coag flip-flop 40 (FIG. 8) so that the Q output of the flip-flop is low and the Q output is high. This indicates operation in the Coagulate mode. The microprocessor then cycles through the IS UP/DOWN SWITCH PRESSED and IS FIRST TIME THRU FLAG CLEARED blocks in the same manner as in the COAG routine. If the microprocessor determines that the up/down switch is depressed, it executes the UP/DOWN routine functions. In the CUT routine, the microprocessor enters the IS COAG PEDAL PRESSED block (FIG. 16B) to determine whether the surgeon has switched from the cut to coagulation mode by releasing the cut pedal and depressing the coag pedal. If the microprocessor determines that the coag pedal is depressed, it transfers to the COAG routine. If the microprocessor determines that the coag pedal is not depressed, it proceeds to the IS CUT PEDAL PRESSED block (FIG. 16C). If the microprocessor determines that the cut pedal remains depressed, it returns to the IS UP/DOWN SWITCH PRESSED block and repeats the foregoing functions. If the microprocessor determines that the cut pedal has been released, it returns to the MAIN routine.

As previously indicated, if the microprocessor determines that neither the coag pedal nor the cut pedal are depressed while in the MAIN routine, it enters the IS UP/DOWN SWITCH PRESSED block. If the microprocessor determines that the up/down switch is depressed, it enters the UP/DOWN routine so as to obtain the desired power setting before operation is initiated in either mode.

The UP/DOWN routine is shown in FIGS. 16A-C. In the UP/DOWN routine, the microprocessor waits 10 milliseconds and then enters the IS SWITCH SET TO UP block. The microprocessor generates the MWR and N7 signals to enable the status input control 212 to transmit the up/down Direction signal to the BUS 0 input of the microprocessor. If the Direction signal indicates that the power switch is in the up position, the microprocessor enters the IS INDEX REG AT TOP block. The microprocessor determines whether the lookup table in EPROM 142 is being addressed at the "top" address corresponding to the maximum power setting. If so, the microprocessor does not increment the index register but, instead, proceeds directly to call the LOOKUP, DISPLAY, DAC and TALK routines. If the index register is not at the "top" EPROM power setting address, the microprocessor increments the index register to the EPROM address for the next higher power setting. The microprocessor then calls the LOOKUP, DISPLAY, DAC and TALK routines.

If the microprocessor determines that the power switch is in the "down" position, it proceeds directly from the IS SWITCH SET TO UP block to the IS INDEX REG AT BOTTOM block. The microprocessor determines whether the index register is addressing the "bottom" address of the EPROM lookup table corresponding to the minimum or zero power setting. If the index register is pointing to the "bottom" address, the microprocessor calls the LOOKUP, DISPLAY, DAC and TALK routines. If the microprocessor determines that the index register is not pointing to the "bottom" address so that the power setting is not at the minimum level, the microprocessor decrements the index register so that the register points to the next lower lookup table address corresponding to the next lower power setting. The microprocessor then proceeds to the LOOKUP, DISPLAY, DAC and TALK routines.

When the microprocessor completes the TALK routine, while in the UP/DOWN routine, it returns to the IS UP/DOWN SWITCH PRESSED block in the MAIN routine to determine whether the up/down switch has been released. See FIGS. 16B-C. If the switch has been released, the microprocessor returns to the beginning of the MAIN routine. If the switch remains depressed, in either the "up" or "down" position, the microprocessor returns to the UP/DOWN routine and executes the functions previously described.

During any of the above routines, the microprocessor may receive an externally generated Interrupt signal from Interrupt circuit 234 in response to a No B++ Detect signal (FIG. 15). The No B++ Detect signal indicates an open fuse F4 due to overcurrent at the power supply B++ output as previously explained. Upon receipt of the Interrupt signal, the microprocessor enters the INTERRUPT routine (FIG. 17A-B.) In this routine, the microprocessor sets the microprocessor Q output signal low so as to cut off the RF power output waveform and it transmits data over the data bus lines to the speech synthesizer processor 170 so that the processor 170 retrieves an error message from EPROM 172. The processor uses the error message to generate a voice message "Internal Fuse" which is sounded by the speaker 196. The microprocessor then enters a "FLASH 00" loop. In the FLASH 00 loop, the microprocessor blanks the display 16, waits 160 miliseconds, transmits data on the data bus lines to display to cause the display to display the error message "00", waits 320 milliseconds and repeats the foregoing operations. When the external Interrupt is removed, upon replacement of the fuse F4, the microprocessor resumes the operation which it had temporarily discontinued upon receipt of the external Interrupt signal.

The present invention may be embodied in other specific forms without departing from the spirit or essential attributes thereof and, accordingly, reference should be made to the appended claims, rather than to the foregoing specification, as indicating the scope of the invention.

We claim:

1. Electrosurgical apparatus, comprising:
   a bipolar electrode,
   means for electronically synthesizing an aperiodic sequence of uniform-width bursts of a high frequency signal,
   means for impressing substantially identical decaying amplitude envelopes on said bursts, each of said envelopes having a predetermined rate of change from a preselected initial amplitude, and
   means for applying said impressed bursts to said electrode.

2. Electrosurgical apparatus according to claim 1 including means for varying the frequency of said high frequency signal within said bursts.

3. Electrosurgical apparatus according to claim 2 including means for varying the frequency of said high frequency signal between preset frequency limits.

4. Electrosurgical apparatus according to claim 3 including circuitry to cause said preset frequency limits to be 0.96 MHz and 1.04 MHz.

5. Electrosurgical apparatus according to claim 1 including means for varying the power of said sequence of bursts by varying the amplitudes of said envelopes.

6. Electrosurgical apparatus according to claim 5 including means for displaying a number representative of the power of said sequence of bursts.

7. Electrosurgical apparatus according to claim 5 including means for generating a voice signal representative of the power of said sequence of bursts.

8. Electrosurgical apparatus according to claim 1 including means for monitoring the aperiodicity of said sequence of bursts, and means for determining whether the aperiodicity is outside an acceptable limit.

9. Electrosurgical apparatus according to claim 8 including means for displaying an error message if said aperiodicity is outside said limit.

10. Electrosurgical apparatus according to claim 8 including means for sounding an error message if said aperiodicity is outside said limit.

11. Electrosurgical apparatus according to claim 1 including means for detecting whether the power of said sequence of bursts is outside an acceptable power limit, and means for automatically terminating said sequence of bursts if said power is outside the power limit.

12. Electrosurgical apparatus according to claim 11 including means for displaying an error message if said power is outside said power limit.

13. Electrosurgical apparatus according to claim 11 including means for sounding an error message if said power is outside said power limit.

14. Electrosurgical apparatus according to claim 1 including means for varying the inter-burst spacing between 11-51 microseconds.

15. Electrosurgical apparatus according to claim 1 including means for modulating said aperiodic sequence of bursts so that said bursts recur aperiodically over regularly occuring repetitive intervals of time of preselected duration separated by dead zones of preselected duration in which the bursts are absent.

16. Electrosurgical apparatus according to claim 15 including circuitry for causing said preselected intervals of time to be 6 milliseconds long and said dead zones to be 3 milliseconds long.

17. Electrosurgical apparatus according to claim 15 including means for preventing modulation of said bursts due to regular occurrence of said dead zones.

18. Electrosurgical apparatus according to claim 15 including means for preventing an abrupt rise of said burst envelope prior to decay.

19. Electrosurgical apparatus according to claim 1 including circuitry for causing the frequency of said high frequency signal to be approximately 1 MHz.

20. Electrosurgical apparatus according to claim 1 including forceps adatped for electrical connection to said means for generating said aperiodic sequence of bursts.

21. Electrosurgical apparatus according to claim 1 including means for delivering said aperiodic sequence of bursts having said decay amplitude envelopes to a load impedance, said load impedance being variable over a substantially wide range of impedances, and means for maintaining the power of said aperiodic sequence of bursts delivered to said load impedance substantially uniform over said range of impedances.

22. Electrosurgical apparatus according to claim 21 wherein said means for delivering said a periodic sequence of bursts includes a step down cup core transformer.

23. Electrosurgical apparatus comprising:
a bipolar electrode,
means for electronically synthesizing an aperiodic sequence of uniform-width bursts of a high frequency signal, means for impressing substantially identical predetermined decaying amplitude envelopes on said bursts, each of said envelopes having a predetermined rate of change from a preselected initial amplitude,
means for varying the frequency of said high frequency signal within said bursts, and
means for applying said impressed bursts to said electrode.

24. Electrosurgical apparatus according to claim 23 including means for varying the power of said sequence of bursts by varying the amplitudes of said envelopes.

25. Electrosurgical apparatus according to claim 24 including means for displaying a number representative of the power of said sequence of bursts.

26. Electrosurgical apparatus according to claim 24 including means for generating a voice signal representative of the power of said sequence of bursts.

27. Electrosurgical apparatus according to claim 23 including means for monitoring the aperiodicity of said sequence of bursts, and means for determining whether the aperiodicity is outside an acceptable limit.

28. Electrosurgical apparatus according to claim 27 including means for displaying an error message if said aperiodicity is outside said limit.

29. Electrosurgical apparatus according to claim 27 including means for sounding an error message if said aperiodicity is outside said limit.

30. Electrosurgical apparatus according to claim 23 including means for detecting whether the power of said sequence of bursts is outside an acceptable power limit and means for automatically terminating said sequence of bursts if said power is outside the power limit.

31. Electrosurgical apparatus according to claim 30 including means for displaying an error message if said power is outside said power limit.

32. Electrosurgical apparatus according to claim 30 including means for sounding an error message if said power is outside said power limit.

33. Electrosurgical apparatus according to claim 23 including means for varying the inter-burst spacing between 11-51 microseconds.

34. Electrosurgical apparatus according to claim 23 including means for modulating said aperiodic sequence of bursts so that said bursts recur aperiodically over regularly occurring repetitive intervals of time of preselected duration separated by dead zones of preselected duration in which the bursts are absent.

35. Electrosurgical apparatus according to claim 34 including circuitry for causing said preselected intervals of time to be 6 milliseconds long and said dead zones to be 3 milliseconds long.

36. Electrosurgical apparatus according to claim 34 including means for preventing modulation of said bursts due to regular occurrence of said dead zones.

37. Electrosurgical apparatus according to claim 34 including means for preventing an abrupt rise of said burst envelope prior to decay.

38. Electrosurgical apparatus according to claim 23 including circuitry for causing the frequency of said high frequency signal to be approximately 1 MHz.

39. Electrosurgical apparatus according to claim 23 including circuitry for causing the frequency of said high frequency signal to vary between the preset frequency limits.

40. Electrosurgical apparatus according to claim 39 including circuitry for causing said preset frequency limits to be 0.96 MHz and 1.04 MHz.

41. Electrosurgical apparatus according to claim 23 including forceps adapted for electrical connection to said means for generating said aperiodic sequence of bursts.

42. Electrosurgical apparatus according to claim 23 including means for delivering said aperiodic sequence of bursts having said decay amplitude envelopes to a load impedance, said load impedance being variable over a substantially wide range of impedance, and means for maintaining the power of said aperiodic sequence of bursts delivered to said load impedance substantially uniform over said range of impedances.

43. Electrosurgical apparatus according to claim 42 wherein said means for delivering said aperiodic sequence of bursts includes a step down cup core transformer.

44. Electrosurgical apparatus, comprising:
a bipolar electrode,
manually actuable means for generating a mode signal indicative of whether the appartus is to operate in a coagulate mode or in a cut mode,
means for electronically synthesizing an aperiodic sequence of uniform-width bursts of a high frequency signal when said mode signal indicates operation in the coagulate mode, said bursts having substantially identical decaying amplitude envelopes, each of said envelopes having a predetermined rate of change from a preselected initial amplitude,
means for varying the frequency of said high frequency signal within said bursts,
means for generating a continuous, substantially uniform amplitude high frequency signal when said mode signal indicates operation in the cut mode, and
means for selectably applying said bursts and said uniform aplitude high frequency signal to said electrode.

45. Electrosurgical apparatus according to claim 44 wherein said manually actuable means includes footpedal means comprising a manually actuable coag pedal for generating a mode signal indicative of operation in the coagulate mode, and a manually actuable cut pedal for generating a mode signal indicative of the cut mode, and means for generating a mode signal indicative of operation in the coagulate mode if said coag and cut pedals are simultaneously actuated.

46. Electrosurgical apparatus according to claim 44 including means for automatically setting the amplitude of said continuous high frequency signal at a first level if said mode signal indicates operation in the cut mode and for automatically setting the initial amplitude of each of said burst envelopes at a second, higher level if said mode signal indicates operation in the coagulate mode.

47. Electrosurgical apparatus according to claim 44 including manually actuable means for varying the power of said sequence of bursts or the power of said continuous high frequency signal by varying the amplitudes thereof.

48. Electrosurgical apparatus according to claim 44 including means for displaying a number representative of the power of said sequence of bursts or the power of said continuous high frequency signal.

49. Electrosurgical apparatus according to claim 48 including means for sounding said number.

50. Electrosurgical apparatus accordingto claim 44 including means for monitoring the aperiodicity of said sequence of bursts, and means for determining whether the aperiodicity is outside an acceptable limit.

51. Electrosurgical apparatus according to claim 50 including means for displaying an error message if said aperiodicity is outside said limit.

52. Electrosurgical apparatus according to claim 50 including means for sounding an error message if said aperiodicity is outside said limit.

53. Electrosurgical apparatus according to claim 44 including means for detecting whether the power of said sequence of bursts or the power of said continuous, high frequency signal is outside an acceptable power limit, and means for automatically terminating said sequence of bursts or said continuous, high frequency signal if said power is outside the power limit.

54. Electrosurgical apparatus according to claim 53 including means for displaying an error message if said power is outside said power limit.

55. Electrosurgical apparatus according to claim 53 including means for sounding an error message if said power is outside said power limit.

56. Electrosurgical apparatus according to claim 44 including means for varying the inter-burst spacing varies between 11–51 microseconds.

57. Electrosurgical apparatus according to claim 44 including means for modulating said aperiodic sequence of bursts so that said bursts recur aperiodically over regularly occurring repetitive intervals of time of preselected duration separated by dead zones of preselected duration in which the bursts are absent.

58. Electrosurgical apparatus according to claim 57 including circuitry for causing said preselected intervals of time to be 6 milliseconds long and said dead zones to be 3 milliseconds long.

59. Electrosurgical apparatus according to claim 57 including means for preventing modulation of said bursts due to regular occurrence of said dead zones.

60. Electrosurgical apparatus according to claim 57 including means for preventing an abrupt rise of said burst envelope prior to decay.

61. Electrosurgical apparatus according to claim 44 including circuitry for causing the frequency of said high frequency signal within said bursts to be approximately 1 MHz.

62. Electrosurgical apparatus according to claim 44 including circuitry for causing the frequency of said high frequency signal within said bursts to vary between preset frequency limits.

63. Electrosurgical apparatus according to claim 62 including circuitry for causing said preset frequency limits to be 0.96 MHz and 1.04 MHz.

64. Electrosurgical apparatus according to claim 44 including forcep means adapted for electrical connection to said means for generating aperiodic sequence of bursts or said continuous, high frequency signal.

65. Electrosurgical apparatus according to claim 44 including means for delivering said aperiodic sequence of bursts having said decay amplitude envelopes to a load impedance, said load impedance being variable over a substantially wide range of impedances, and means for maintaining the power of said aperiodic sequence of bursts delivered to said load impedance substantially uniform over said range of impedances.

66. Electrosurgical apparatus according to claim 65 wherein said means for delivering said aperiodic sequence of bursts includes a step down cup core transformer.

67. Electrosurgical apparatus comprising:
a bipolar electrode,
means for electronically synthesizing a sequence of aperiodic trigger pulses,
means for electronically synthesizing a burst of ramped high frequency pulses in response to each of said trigger pulses, said high frequency pulses having successive amplitudes which decrease at a predetermined rate,
means for electronically synthesizing a damped high frequency sinusoidal signal in response to each of said bursts of ramped high frequency pulses, and
means for applying said damped high frequency sinusoidal signal to said electrode.

68. Electrosurgical apparatus according to claim 67 wherein said means for generating said burst of ramped pulses includes means for generating a sequence of multiple bit digital signals of decreasing value in response to each of said trigger pulses, and means for converting each multiple bit digital signal into an analog pulse.

69. Electrosurgical apparatus according to claim 67 including means for varying the frequency of said pulses within said burst.

70. Electrosurgical apparatus according to claim 69 wherein said means for varying the frequency of said pulses includes a phase locked loop in phase coherence with said means for generating said burst of ramped pulses.

71. Electrosurgical apparatus according to claim 69 including means for varying the frequency of said ramped pulses between preset frequency limits.

72. Electrosurgical apparatus according to claim 71 including circuitry for causing said preset frequency limits to be 0.96 MHz and 1.04 MHz.

73. Electrosurgical apparatus according to claim 67 including circuitry for causing the spacing between consecutive bursts of ramped analog pulses to be based on the spacing between consecutive trigger pulses, and for causing said spacing between consecutive trigger pulses to vary between 11–51 microseconds.

74. Electrosurgical apparatus according to claim 67 wherein said means for generating said aperiodic sequence of trigger pulses includes means for generating said sequence over repetitive regularly occurring intervals of time of preselected duration separated by dead zones of preselected duration during which said trigger pulses are not generated.

75. Electrosurgical apparatus according to claim 75 including circuitry for causing said intervals of time of preselected duration to be 6 milliseconds long and said dead zones to be 3 milliseconds long, 76. Electrosurgical apparatus, comprising:
a bipolar electrode,
means for electronically synthesizing an aperiodic sequence of uniform-width bursts of a damped high frequency sinusoidal voltage signal,
means for varying the frequency of said high frequency sinusoidal voltage signal within the bursts, and
means for applying said bursts to said electrode.

77. Electrosurgical apparatus according to claim 76 wherein said means for varying said frequency includes means for varying the frequency between preset frequency limits.

78. Electrosurgical apparatus according to claim 76 wherein said means for varying said frequency includes a phase locked loop in phase coherence with said means for generating said aperiodic sequence of bursts.

79. Electrosurgical apparatus according to claim 77 including circuitry for causing said preset frequency limits to be 0.96 MHz and 1.04 MHz.

80. Electrosurgical method of coagulating vessels, tissue, or the like, comprising:
generating a power signal at bipolar forceps, said power signal comprising an aperiodic sequence of uniform-width bursts of a high frequency signal,
impressing substantially identical decaying amplitude envelope on said bursts, each of said envelopes having a predetermined rate of change from a preselected initial amplitude, and
applying said forceps to said vessels, tissue or the like.

81. Electrosurgical method according to claim 80 including varying the frequency of said high frequency signal within said bursts.

82. Electrosurgical method according to claim 81 including varying the frequency of said high frequency signal between preset frequency limits.

83. Electrosurgical method accordingto claim 82 wherein said preset frequency limits are 0.96 Mhz and 1.04 Mhz.

84. Electrosurgical method according to claim 80 wherein the inter-burst spacing varies between 11–55 microseconds.

85. Electrosurgical method according to claim 80 including modulating said aperiodic sequence of bursts so that said bursts recur aperiodically over regularly occurring repetitive intervals of time of preselected duration separated by dead zones of preselected duration in which the bursts are absent.

86. Electrosurgical method according to claim 85 wherein said preselected intervals of time are 6 milliseconds long and said dead zones are 3 milliseconds long.

87. Electrosurgical method of coagulating vessels, tissue and the like, comprising:
generating a power signal at bipolar forceps, said power signal comprising an aperiodic sequence of uniform width bursts of a high frequency signal,
impressing substantially identical decaying amplitude envelope on said bursts, each of said envelopes having a predetermined rate of change from a preselected initial amplitude,
varying the frequency of said high frequency signal within said bursts, and
applying said forceps to said vessels, tissue or the like.

88. Electrosurgical method according to claim 87 including varying the frequency of said high frequency signal between preset frequency limits.

89. Electrosurgical method according to claim 88 wherein said preset frequency limits are 0.96 Mhz and 1.04 Mhz.

90. Electrosurgical method according to claim 87 wherein the inter-burst spacing varies between 11–51 microseconds.

91. Electrosurgical method according to claim 87 including modulating said aperiodic sequence of bursts so that said bursts recur aperiodically over regularly occurring repetitive intervals of time of preselected duration separated by dead zones of preselected duration in which the bursts are absent.

92. Electrosurgical method according to claim 91 wherein said preselected intervals of time are 6 milliseconds long and said dead zones are 3 milliseconds long.

* * * * *